US007270996B2

(12) United States Patent
Cannon et al.

(10) Patent No.: US 7,270,996 B2
(45) Date of Patent: Sep. 18, 2007

(54) AUTOMATED BIOCULTURE AND BIOCULTURE EXPERIMENTS SYSTEM

(76) Inventors: Thomas F. Cannon, 4020 Roxmill Ct., Glenwood, MD (US) 21738; Laura K. Cohn, 2457 N. Stevens St., Alexandria, VA (US) 22311; Peter D. Quinn, 1921 17th St., NW., Washington, DC (US) 20009

( * ) Notice: Subject to any disclaimer, the term of this patent is extended or adjusted under 35 U.S.C. 154(b) by 0 days.

(21) Appl. No.: 09/967,995

(22) Filed: Oct. 2, 2001

(65) Prior Publication Data
US 2002/0055166 A1    May 9, 2002

Related U.S. Application Data

(60) Provisional application No. 60/236,733, filed on Oct. 2, 2000, provisional application No. 60/236,702, filed on Oct. 2, 2000, provisional application No. 60/236,703, filed on Oct. 2, 2000.

(51) Int. Cl.
*C12M 3/00* (2006.01)
*C12M 1/34* (2006.01)

(52) U.S. Cl. .................. 435/293.1; 435/3; 435/33; 435/325; 435/286.5; 435/303.1; 435/309.2; 435/809

(58) Field of Classification Search .................. 435/29, 435/3, 32, 33, 286.5, 286.6, 287.1, 293.1, 435/297.2, 297.4, 297.5, 303.1, 309.1, 309.2, 435/809
See application file for complete search history.

(56) References Cited

U.S. PATENT DOCUMENTS 4,087,327 A    5/1978 Feder et al.
4,201,845 A *  5/1980 Feder et al. ............. 435/297.2
4,212,845 A *  7/1980 Stelling et al. ............... 422/82

(Continued)

FOREIGN PATENT DOCUMENTS

WO    WO97/16527    5/1997

(Continued)

OTHER PUBLICATIONS

*Aastrom Biosciences, Inc.*, Annual Report 2001.

(Continued)

*Primary Examiner*—William H Beisner
(74) *Attorney, Agent, or Firm*—Thelen Reid Brown Raysman & Steiner LLP

(57) ABSTRACT

The present invention provides a feedback controlled bioculture platform for use as a precision cell biology research tool and for clinical cell growth and maintenance applications. The system provides individual closed-loop flowpath cartridges, with integrated, aseptic sampling and routing to collection vials or analysis systems. The system can operate in a standard laboratory or other incubator for provision of requisite gas and thermal environment. System cartridges are modular and can be operated independently or under a unified system controlling architecture, and provide for scale-up production of cell and cell products for research and clinical applications. Multiple replicates of the flowpath cartridges allow for individual, yet replicate cell culture growth and multiples of the experiment models that can be varied according to the experiment design, or modulated to desired cell development of cell culture end-points. The integral flowpath cartridge aseptic sampling system provides for dynamic analysis of metabolic products or representative cells from the culture.

95 Claims, 17 Drawing Sheets

U.S. PATENT DOCUMENTS

| | | | |
|---|---|---|---|
| 4,228,242 | A | 10/1980 | Girard et al. |
| 4,242,459 | A | 12/1980 | Chick et al. |
| 4,246,120 | A | 1/1981 | Baudet et al. |
| 4,310,630 | A | 1/1982 | Girard et al. |
| 4,311,798 | A | 1/1982 | Katinger et al. |
| 4,391,912 | A | 7/1983 | Yoshida et al. |
| 4,440,853 | A | 4/1984 | Michaels et al. |
| 4,442,206 | A | 4/1984 | Michaels et al. |
| 4,537,860 | A | 8/1985 | Tolbert et al. |
| 4,546,083 | A | 10/1985 | Meyers et al. |
| 4,647,539 | A | 3/1987 | Bach |
| 4,649,114 | A | 3/1987 | Miltenburger et al. |
| 4,650,766 | A * | 3/1987 | Harm et al. ............. 435/286.6 |
| 4,722,902 | A * | 2/1988 | Harm et al. ............. 435/297.4 |
| 4,748,124 | A | 5/1988 | Vogler |
| 4,808,315 | A | 2/1989 | Manabe et al. |
| 4,889,812 | A | 12/1989 | Guinn et al. |
| 4,942,770 | A * | 7/1990 | Seifert et al. ............ 73/864.34 |
| 4,999,298 | A | 3/1991 | Wolfe et al. |
| 4,999,307 | A | 3/1991 | Oakley |
| 5,081,035 | A | 1/1992 | Halberstadt et al. |
| 5,202,254 | A | 4/1993 | Amiot et al. |
| 5,270,192 | A * | 12/1993 | Li et al. .................... 435/174 |
| 5,338,662 | A | 8/1994 | Sadri |
| 5,368,555 | A | 11/1994 | Sussman et al. |
| 5,416,022 | A | 5/1995 | Amiot |
| 5,424,209 | A | 6/1995 | Kearney |
| 5,427,266 | A * | 6/1995 | Yun ............................ 220/377 |
| 5,494,822 | A | 2/1996 | Sadri |
| 5,612,188 | A | 3/1997 | Shuler et al. |
| 5,656,421 | A | 8/1997 | Gebhard et al. |
| 5,688,687 | A | 11/1997 | Palsson et al. |
| 5,792,603 | A | 8/1998 | Dunkelman et al. |
| 5,866,420 | A * | 2/1999 | Talbot et al. ................ 435/395 |
| 5,985,653 | A | 11/1999 | Armstrong et al. |
| 5,989,913 | A | 11/1999 | Anderson et al. |
| 5,994,129 | A | 11/1999 | Armstrong et al. |
| 6,008,010 | A | 12/1999 | Greenberger et al. |
| 6,048,721 | A | 4/2000 | Armstrong et al. |
| 6,096,532 | A | 8/2000 | Armstrong et al. |
| 6,110,212 | A | 8/2000 | Gregory |
| 6,121,042 | A | 9/2000 | Peterson et al. |
| 6,174,719 | B1 | 1/2001 | Elizondo et al. |
| 6,228,635 | B1 | 5/2001 | Armstrong et al. |
| 6,238,908 | B1 | 5/2001 | Armstrong et al. |
| 2002/0146817 | A1 * | 10/2002 | Cannon et al. .......... 435/289.1 |

FOREIGN PATENT DOCUMENTS

| | | |
|---|---|---|
| WO | WO 02/28996 | 4/2002 |

OTHER PUBLICATIONS

*Cell Manufacturing Instruments*, BioVest, http.//www.biovest.com/cmi.html, no date provided.

Synthecon, Inc.—Products, http.//www.synthecon.com/products.shtml, no date provided.

*FiberCell™ Hollow Fiber Cell Culture Systems*, FiberCell Systems, Inc., Hollow Fiber Cell Culture Technology, wysiwyg://129/http://www.fibercellsystems.com/about.htm, no date provided.

FiberCell Systems, Inc., Hollow Fiber Cell Culture Technology, Product Specifications, wysiwyg://136/http://www.fibercellsystems.com/specifications/htm, no date provided.

*CELLMAX® Artificial Capillary Cell Culture Systems*, Cellco Cellmax, http://www.spectrapor.com/cellco/cellmax.html, no date provided.

Abstract, "Re-endothelialization of porcine derived elastin heterografts using porcine aortic endothelial cells, pulsatile perfusion, and controlled shear stress conditions.", Kenton W. Gregory et al., Poster presented at Sixth World Biomaterials Congress, Kamuela, HI, May 2000.

"Elastin As A Matrix For Vascular Cell Repopulation For Stent Coverings And Conduits", Abstract presented at Elastin 2001 Conference, Reims, France, Jul. 2001.

International Search Report in Application PCT/US03/09584 mailed Jul. 14, 2003.

"A Blood Vessel Model Constructed from Collagen and Cultured Vascular Cells", by Crispin B. Weinberg and Eugene Bell, Science, vol. 231, Jan. 1986, pp. 397-400.

"A Completely Biological Tissue-Engineered Human Blood Vessel", by Nicolas L'Heureux, et al., The FASEB Journal, vol. 12, Jan. 1998, pp. 47-56.

"Functional Arteries Grown in Vitro", by L.E. Niklason, et al., Science, vol. 284, Apr. 16, 1999, pp. 489-493.

"Liposuction-Derived Human Fat Used for Vascular Graft Sodding Contains Endothelial Cells and Not Mesothelial Cells as the Major Cell Type", by Stuart K. Williams, PhD., et al., Journal of Vascular Surgery, vol. 19, No. 5, May 1994, pp. 916-923.

"Long-Term Results of Femorotibial Bypass With Vein or Polytetrafluoroethylene", R.D. Sayers, et al., British Journal of Surgery, vol. 85, 1998, pp. 934-938.

"Morphologic and Mechanical Characteristics of Engineered Bovine Arteries", Laura E. Niklason, MD, et al., Journal of Vascular Surgery, vol. 33, No. 3, Mar. 2001, pp. 628-638.

"Optimizing Seeding and Culture Methods to Engineer Smooth Muscle Tissue on Biodegradable Polymer Matrices", by Byung-Soo Kim, et al., Biotechnology and Bioengineering, vol. 57, No. 1, Jan. 5, 1998, pp. 46-54.

"Remodeling of Autologous Saphenous Vein Grafts", by Yi Shi, MD, et al., Circulation, vol. 95, No. 12, Jun. 17, 1997, pp. 2684-2693.

"Scaffolds for Engineering Smooth Muscle Under Cyclic Mechanical Strain Conditions", by Byung-Soo Kim, et al., Journal of Biomechanical Engineering, vol. 122, Jun. 2000, pp. 210-215.

The Role of Crosslinking in Modification of the Immune Response Elicited Against Xenogenic Vascular Acellular Matrices, by David W. Courtman, et al., Journal of Biomed. Mater. Res., vol. 55, 2001, pp. 576-586.

"Use of Cardiac Procedures and Outcomes in Elderly Patients with Myocardial Infarction in the United States and Canada", by Jack V. Tu, MD, et al., The New England Journal of Medicine, vol. 336, No. 21, May 22, 1997, pp. 1500-1505.

International Search Report in Application PCT/US01/30630 mailed Feb. 13, 2002.

* cited by examiner

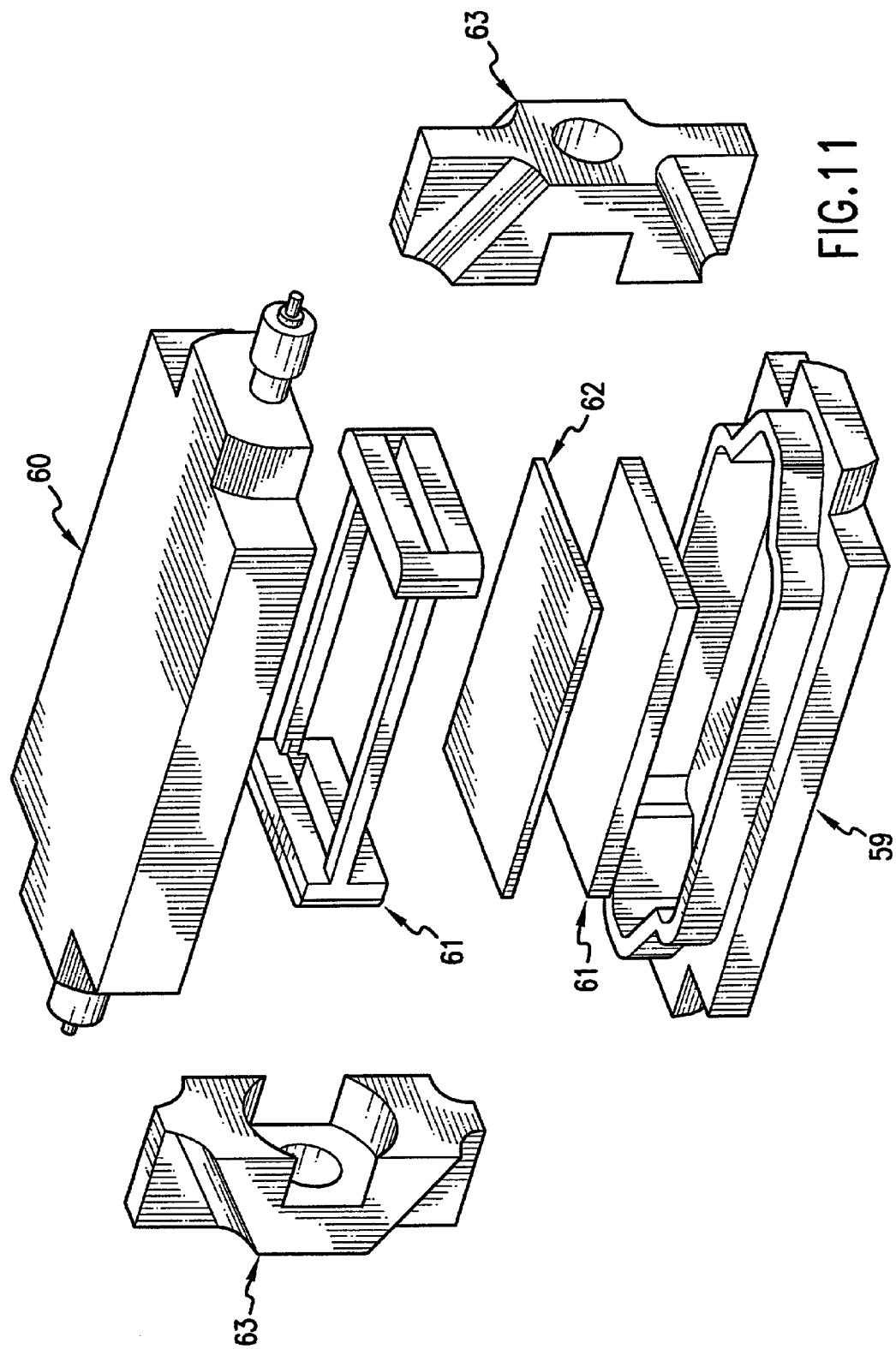

AUTOMATED BIOCULTURE AND BIOCULTURE EXPERIMENTS SYSTEM

This application claims benefit of U.S. Provisional Application Nos. 60/236,733, 60/236,702, and 60/236,703, each filed Oct. 2, 2000.

FIELD OF THE INVENTION

The field of the invention is automated cell culture systems, cell culture growth chambers and automated sampling systems.

BACKGROUND OF THE INVENTION

Cell culture has been utilized for many years in life science research in an effort to better understand and manipulate the cellular component of living systems. Cells are typically grown in a static environment on petri dishes or flasks. These cell culture methods are very labor-intensive especially when a large number of studies need to be performed.

Traditional cell culture systems depend on controlled environments for cell maintenance, growth, expansion, and testing. Typical cell culture laboratories include laminar flow hoods, water-jacketed incubators, controlled access by gowned personnel, and periodic sterilization procedures to decontaminate laboratory surfaces. Personnel require extensive training in sterile techniques to avoid contamination of containers and cell transfer devices through contact with non-sterile materials. Despite these measures, outbreaks of contamination in traditional cell culture laboratories, e.g., fungus or bacterial contamination, commonly occur, often with the impact of compromising weeks of research and halting operations for days or weeks.

Trained technicians under a sterile, laminar flow hood typically perform cell culture. Cells are grown in flasks or bioreactors and maintained in incubators that provide the requisite thermal and gas environment. Cultures are removed from incubators and transported to a sterile hood for processing. Cells can be harmed when removed from their thermal and gas environment. The constant transport and manipulation of the culture represents an opportunity for contamination that can cause weeks of work to be wasted from a single bacterium. Traditional cell culture is very labor intensive and uses a steady stream of sterile, disposable products for each experiment. The nutrient cell culture medium includes a color indicator that is visually inspected by the technician on a daily basis, at a minimum. When the color is deemed to indicate that the pH is falling out of healthy range the cells are removed from the incubator, the old media is manually removed and fresh media is injected. This process is adequate at best.

Perfusion systems provide a three-dimensional cell culture environment that reproduces critical aspects of the dynamic in vivo environment. In vitro perfusion systems allow tissue-engineered cells to develop and organize as if inside the body. Biotechnology companies, universities, and research institutes are attempting to develop complex tissue replacements including liver, pancreas, and blood vessels, among others. These complicated tissue products require advanced biochamber perfusion systems that are capable of mimicking in vivo development dependent stimulation. A perfusion cell culture system's primary purpose is to provide a pump that will continuously re-circulate medium. Standard experiment manipulations, such as media replacement (when it is no longer at the proper pH), cell and media sampling, and fluid injections, are performed by a laboratory technician in a sterile hood. In an age where genetically engineered products will be FDA approved and drug compound costs are hundreds of millions of dollars, the traditional way of performing cell culture is no longer acceptable.

One critical issue to be addressed in any cell culture application involves precision reproducibility and the elimination of site-to-site differences so that cell products and experiments will be consistent in different biochambers or different physical locations. This is particularly difficult to accomplish when culture viability is determined solely on visual cues, i.e., medium color and visualization under a microscope.

In a purely manual environment, quality control is accomplished by selecting qualified personnel, providing them with extensive training, and developing a system of standard operating procedures and documentation. In an automated environment, the principles of process validation are used to demonstrate that the process is precise, reliably consistent, and capable of meeting specifications. The principles of statistical process control are then implemented to monitor the process to assure consistent conformance to specifications.

The particular physical and biological requirements for the growth and modification of cells and tissues of interest vary. However, two key components are necessary in order to grow any of these cells and tissues: cells that are capable of replicating and differentiating, as needed, and an in vitro system containing biocompatible materials that provide for the physiological requirements for the cells to grow, such as surface attachment, medium exchange, and oxygenation. These systems should be automated and amenable for routine use by the thousands of research laboratories, universities, tissue engineering companies, hospitals, and clinics that perform research requiring consistent and reliable results and also those that serve patients intended to benefit from transplantation cells and tissues in native or genetically altered form without adversely affecting product quality and, particularly, product sterility.

Cell and organ transplantation therapy to date has typically relied on the clinical facility to handle and process cells or tissues through the use of laboratory products and processes governed to varying degrees by standard operating procedures and with varying regulatory authority involvement. The procedures to date, however, generally have not required extensive manipulation of the cells or tissue beyond providing short term storage or containment, or in some cases, cryopreservation. With the addition of steps that require the actual growth and production of cells or tissues for transplantation, medium replacement, sampling, injections of drug/compound dosing, physiologic and set-point monitoring, and quality assurance data collection, there are many considerations that need to be addressed in order to achieve a reliable and clinically safe process. This issue is the same regardless of whether the cell production is occurring at the patient care location, as might be the case for the production of cells for a stem cell transplant, or at a distant manufacturing site, as might be the case for organ and tissue engineering applications.

Platform-operated culture systems, typically referred to as bioreactors, have been commercially available. Of the different bioreactors used for mammalian cell culture, most have been designed to allow for the production of high density cultures of a single cell type. Typical application of these high density systems is to produce a conditioned medium produced by the cells. This is the case, for example, with hybridoma production of monoclonal antibodies and with packaging cell lines for viral vector production. These applications differ, however, from applications in which the end-product is the harvested tissue or cells themselves. While traditional bioreactors can provide some economies of labor and minimization of the potential for mid-process contamination, the set-up and harvest procedures involve labor requirements and open processing steps, which require laminar flow hood operation (such as manual media sampling to monitor cell growth). Some bioreactors are sold as large benchtop environmental containment chambers to house the various individual components that must be manually assembled and primed. Additionally, many bioreactor designs impede the successful recovery of expanded cells and tissues and also can limit mid-procedure access to cells for purposes of process monitoring. Many require the destruction of the bioreactor during the harvesting process.

It should therefore be appreciated that within tissue engineering companies, cellular therapeutic companies, research institutions, and pharmaceutical discovery companies there is a need for an automated cell and tissue culture system that can maintain and grow selected biological cells and tissues without being subject to many of the foregoing deficiencies. There also is a need for a lower cost, smaller, automated research and development culture system which will improve the quality of research and cell production and provide a more exact model for drug screening.

SUMMARY OF THE INVENTION

The present invention provides a precision bioculture support system, including a cell culture apparatus for use within an incubator. The apparatus preferably includes at least one media flowpath assembly cartridge having an outer shell or housing and affixed thereto, a pump, at least one valve adapted to prevent or divert media flow, a control interface, and a disposable sterile media perfusion flowpath loop. The media perfusion loop is removably attachable to the outer shell without breaching flowpath sterility, and contains, in fluid communication, at least one biochamber, a tubing in contact with the pump, at least one tubing in contact with the valve, a gas permeable membrane exposed to ambient air, and a media reservoir. In a preferred embodiment, each cartridge has a control interface and battery pack or other power source for stand alone operation. In another preferred embodiment, the apparatus further includes an incubator rack that is removably integratable with a plurality of flowpath assembly cartridges without breaching flowpath sterility.

Another embodiment of the invention provides an incubator rack for supporting a plurality of flowpath assembly cartridges. The rack includes, in one embodiment, a plurality of grooves each adapted to support a flowpath cartridge, a plurality of data interface connections for transmitting data between the rack and the cartridges, and a control interface for communication with an external computer.

The invention further provides an automated sampling device having a fluidic pump for transporting a carrier fluid, a valve for diverting an aliquot of sample from a perfusion loop, a means for sterilizing the carrier fluid, and a check valve. The pump, filter, and check valve are connected in series by tubing for transporting the carrier fluid and the diverted sample from the check valve to a sample collection device or analysis instrument.

The invention further provides a biochamber which is convertible for use in static cell culture or in a perfusion apparatus. The biochamber includes a first chamber, a cover, a seal rendering the first chamber removably connectable to the cover and preventing contamination of the cell culture within the biochamber, and at least one insert positioned between the first chamber and the cover, thereby forming a second chamber.

Additional features and advantages of the invention will be set forth in the description which follows and will be apparent from the description or may be learned by practice of the invention.

BRIEF DESCRIPTION OF THE DRAWINGS

FIG. 11 shows an exploded view of a biochamber in accordance with the invention.

DETAILED DESCRIPTION OF THE INVENTION

Reference will now be made in detail to the presently preferred embodiments of the invention which serve to explain the principles of the invention. It is to be understood that the application of the teachings of the present invention to a specific problem or environment will be within the capabilities of one having ordinary skill in the art in light of the teachings contained herein.

The present invention provides an automated precision cell culture system which includes one or a plurality of perfusion loop flowpath cartridges that can be placed in an optional rack or docking station which fits into an incubator. The incubator provides the appropriate gas and thermal environment for culturing the cells as each perfusion loop contains a means for passive diffusion of air from the incubator environment. The system provides for parallel processing and optimization through continuous set point maintenance of individual cell culture parameters as well as automated sampling and injection. The invention further provides a biochamber which is convertible for use as a static cell culture device or in a perfusion loop flowpath cartridge.

As used herein, "cell culture" means growth, maintenance, transfection, or propagation of cells, tissues, or their products.

As used herein, "integratable" means parts or components which are capable of being joined together for operation as a unit for one or more data transfer or other functions.

As used herein, "without breaching flowpath sterility" refers to the closed nature of the perfusion loop which remains intact during various manipulations or movements such that each flowpath assembly perfusion loop can be connected to a cartridge housing, which in turn can be connected to a rack or docking station, disconnected and then reconnected without exposing the internal surfaces of the flowpath to environmental contaminants and without the components of the perfusion loop flowpath losing fluid communication with one another. Thus, the loop itself is preferably a disposable, unitized system that can be removed from the cartridge's outer shell without its components losing fluid communication with one another. Moreover, an individual perfusion loop can be moved or carried throughout a laboratory or other facility, or to a separate lab or facility, as desired for separate testing or analyses while its contents remain sterile.

Figure 1:
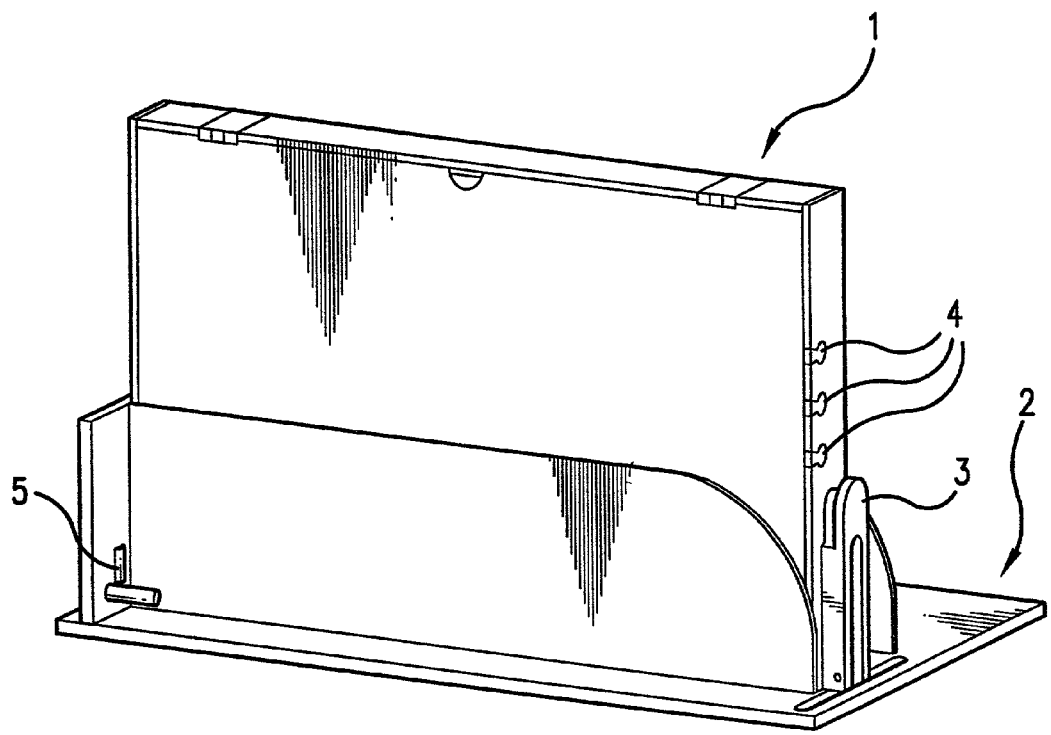
FIG. 1 depicts a media flowpath assembly cartridge and incubator rack in accordance with the invention.

Referring now to FIG. 1, the present invention provides one or a plurality of media flowpath assembly cartridges, 1, which each can be placed into docking station or rack, 2, which can then be placed into a laboratory incubator. The incubator may be any incubating device, and may be located in a laboratory, a manufacturing facility, or any clinical or other setting in which cell culture via incubation is desired. The incubator preferably maintains a controlled environment of about 5% $CO_2$ and about 20% $O_2$ and controlled temperature, although any environment may be used and selected by one of ordinary skill depending on the particular end use application, given the teachings herein. The incubator environment is typically separately controlled, while the automated culture system of the invention is preferably controlled by an external PC for integration of individual flowpath assembly cartridges and system control through a docking station interface, as described in detail below.

The illustrated embodiment of FIG. 1 includes an optional lever 3 for facilitating the cartridge's integration and removal from the rack. In alternate embodiments, a latch or other capture device may be used. The illustrated embodiment also includes optional access ports 4 to accommodate injection or sampling of fluid. One or more connections 5 may also be included for connecting power sources and computer control and data transfer cables.

Figure 2:
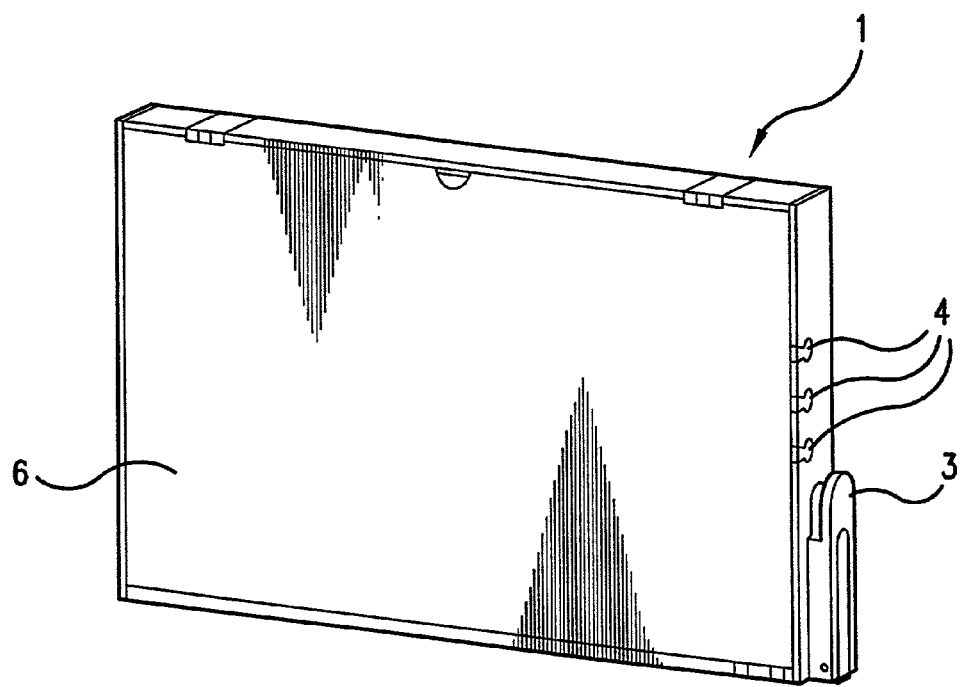
FIG. 2 depicts a media flowpath assembly cartridge in accordance with the invention.
Figure 3:
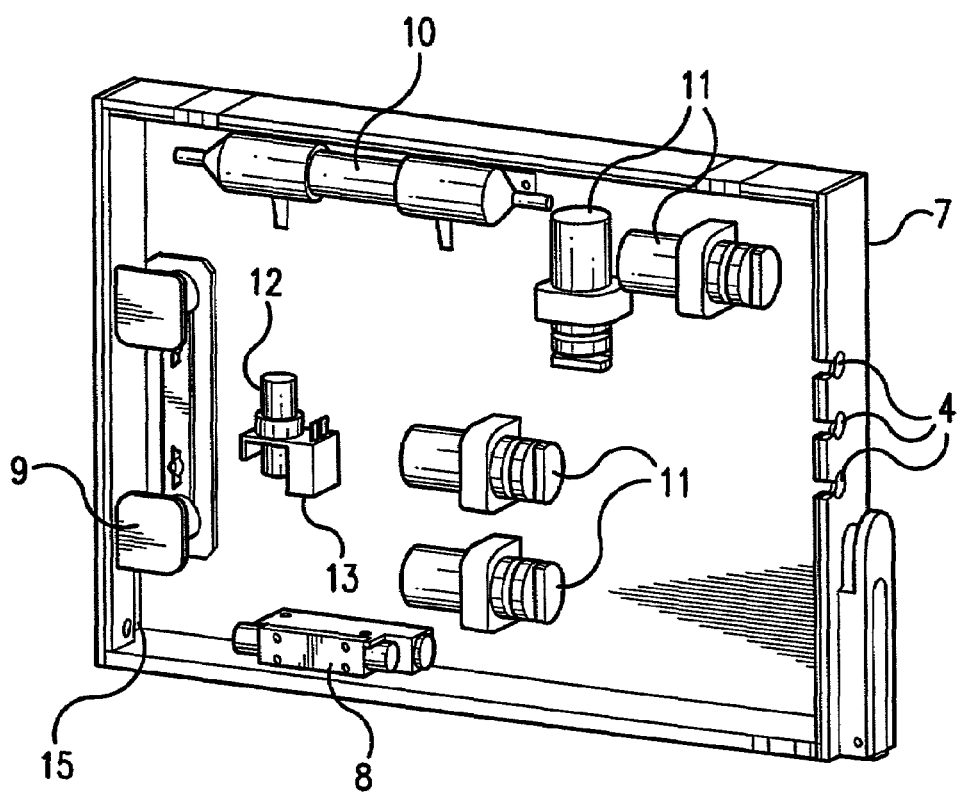
FIG. 3 shows the outer shell of an exemplary cartridge and its fixed components.

FIG. 2 illustrates an embodiment of the invention in which an individual flowpath assembly cartridge is not attached to a rack. In this illustrated embodiment, an optional cover 6 encloses the cartridge's inner components. The cover may be removable and may be connected to the cartridge's outer shell by a hinge. With reference now to FIG. 3, a cartridge outer shell or housing 7 provides physical support for the internal components. The embodiment shown in FIG. 3 illustrates internal hardware components of a preferred cartridge outer shell or housing, including a pump 8, an optional oxygenator bracket 9, a biochamber 10, valves for diverting media flow 11, a flow cell or drip chamber 12, a noninvasive sensor 13, a series of access ports 4, an optional air pump for sample routing 0.1 micron filtered air (not shown in FIG. 3), and an interface 15 for interfacing with a connection located on the rack or with a separate power source. The flow cell or drip chamber may be combined with a noninvasive sensor, for example a pH sensor, to form a single component. In an alternate embodiment, interface 15 may provide a connection for a computer cable for control and data transfer. In another alternate embodiment, interface 15 may provide fluid connection downstream to an inline analyzer. The in-line analyzer may provide data on, for example, cell metabolic activity. Many such in-line analyzers are suitable for use in the present invention.

Figure 4:
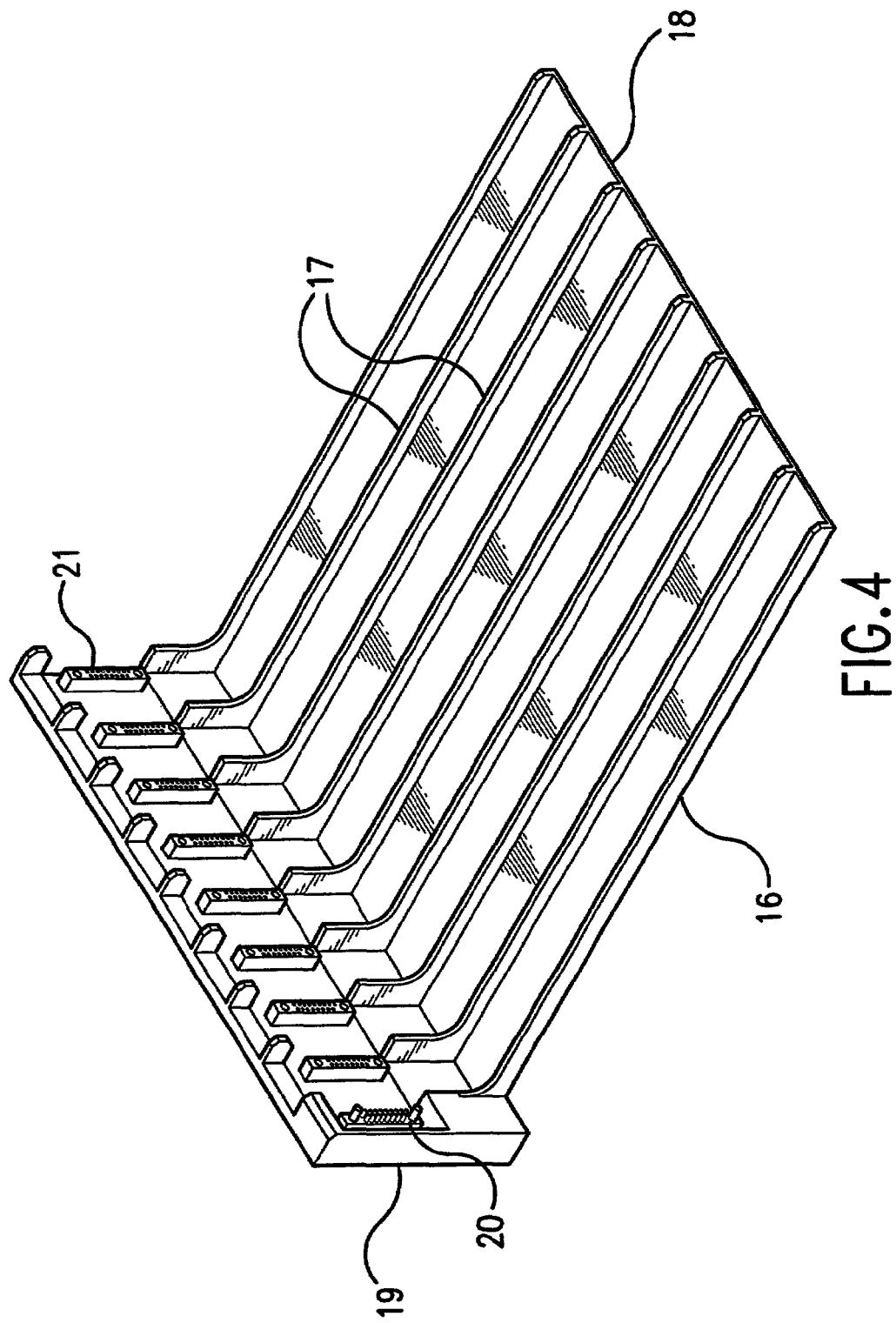
FIG. 4 shows an incubator rack in accordance with the invention.

The incubator rack operates as a docking station for one or preferably multiple cartridges when they are positioned within an incubator during operation of the cell culture system. The rack or docking station is preferably fabricated from a plastic material and may be manufactured by, for example, injection molding. Referring to FIG. 4, in one embodiment the rack has a horizontal base 16 and a series of vertical dividers 17 forming grooves, or tracks 18 for guiding the insertion of and supporting each flowpath assembly cartridge. In one embodiment, the vertical dividers provide a small space between each docked cartridge and its adjacent or neighboring cartridge. The rack may also provide orthogonal support via a vertical wall 19 preferably in the rear of the rack. The rack may also have at least one connector 20 and 21, preferably in the rear and affixed to the vertical wall, for conveying power from a power source and for communication with an external computer. Connectors may also be present for attaching a power or communication cable to a single cartridge or to multiple cartridges operating within the same rack. A series of connectors may optionally be attached to a circuit board laid into a groove in the rear plane of the rack (not shown). The rack may also include a fan for circulating air within the incubator or a vibration isolation and damping system.

To increase portability of a filly loaded rack, an open box structure can be employed which further protects the front section and secures the cartridges for transporting within the rack as a unit. In the embodiment shown in FIG. 4, the rack accommodates eight cartridges. An incubating device suitable for use in accordance with the present invention can accommodate a rack adapted to hold any desired number of cartridges. The rack may thus be manufactured to include as many slots or tracks as can fit into a standard laboratory incubator or other suitable incubating device. A common laboratory incubator will readily support up to ten cartridges or more on one shelf.

A lever action removal mechanism may be included to overcome resistance of the electrical connectors to disengagement and thus facilitate removal of each cartridge from the rack. In another embodiment, an indicator illuminates when a cartridge is properly connected to the electrical connectors or when a cartridge is not receiving power. The indicator is preferably an LED. In a still further embodiment, a battery power source is included on or in the cartridge to provide back up power and power for when the cartridge is transported or otherwise removed from the rack. A handle may be located on each cartridge housing to facilitate its removal from the rack. Such handles can include an indentation for grasping, which may be located in various locations, preferably the top, right-hand side, a foldaway handle, or any other mechanism for facilitating manual transfer and portability of each cartridge. The cartridge's outer shell is preferably made of plastic and may be formed by injection molding. The cartridge may also include a display or control panel. The cartridge may also include a circuit board in one of numerous locations. A preferable location is on or embedded in the back plane of the cartridge's outer shell. In an alternate embodiment, a fold out stand on the bottom plane of the cartridge outer shell may be included. The stand would allow the user to place the cartridge on a desktop once the flow path is inserted and is an aid to keep the cartridge in a vertical position during some phases of sterile processing in the sterile hood. Prior to inserting the cartridge into the rack, the stand can be rotated 90 degrees into a tucked away position. Any other stand or suitable mechanism capable of providing support on a table or bench, or other horizontal surface for an individual cartridge can be used, if desired.

In one embodiment, cartridges may be integrated such that two or more flowpaths are in fluid connection with each other for conducting experiments. This embodiment is advantageous when, for example, increased fluid volume, increased cell volume, or cell co-culture is desired. Cell co-culture includes culturing a different cell type in each cartridge. In an alternate embodiment, larger cartridges with increased biochamber and media supply are accommodated for scaled up cell culture.

Figure 5:
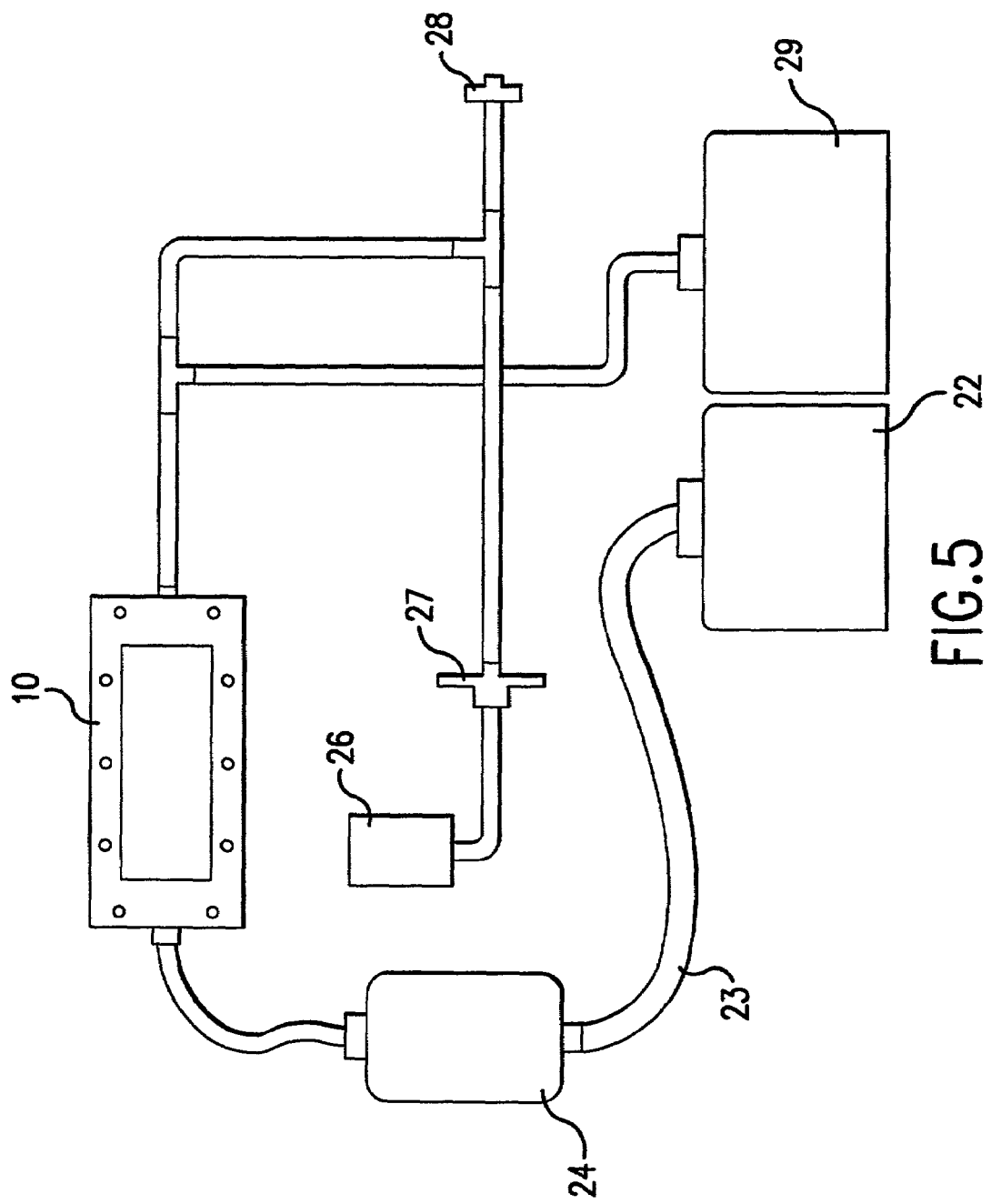
FIG. 5 shows a unitized, disposable flowpath perfusion loop in accordance with the invention.

The invention further provides a unitized, disposable sterile media perfusion loop flowpath, which is removably attachable to the outer shell or housing of the cartridge without breaching flowpath sterility. The perfusion loop is preferably a continuous flow perfusion loop, but can also function as a single pass perfusion loop. In an alternate embodiment, the perfusion loop is a single pass perfusion loop. The loop is preferably removable from the cartridge housing as a single disposable unit. FIG. 5 illustrates one embodiment of a unitized perfusion loop according to the invention. In FIG. 5, the loop is not connected to a cartridge. As shown in the embodiment of FIG. 5, the media perfusion loop or flowpath includes a media reservoir 22, tubing 23, an oxygenator 24, a biochamber or bioreactor 10, an interface to accommodate an air supply 26 for sample removal, a filter 27 for sterilizing air from the air supply, a sampling interface 28, and a waste reservoir 29 (injection and sample reservoirs not shown in this Fig.). In an alternate embodiment, the flowpath includes an interface for connection with an analyzer. The oxygenator 24 is preferably a passive diffusion oxygenator. The oxygenator may comprise any gas permeable surface. In an alternate embodiment, the oxygenator is a diffusion membrane positioned, for example, over a valve manifold. In another alternate embodiment, the oxygenator is a diffusion membrane positioned over the biochamber. Alternatively, the oxygenator may be a hollow fiber for accommodating forced gas.

In an alternate embodiment, more than one biochamber or bioreactor is included in a single flowpath for increasing cell volume or to provide co-culturing. The biochambers may be connected in series or in parallel. Waste contained in the waste reservoir 29 may include spent media, cellular byproducts, discarded cells, or any other component that enters the waste reservoir 29 through the media perfusion loop. Sampling interface 28 may be any suitable connection or surface forming a boundary through which a sample may be extracted from the perfusion loop while eliminating or minimizing any potential breach in flowpath sterility. Extraction may be manual or automated. The sampling interface may, for example, be a silicon injection site or a lure connection.

Figure 6:
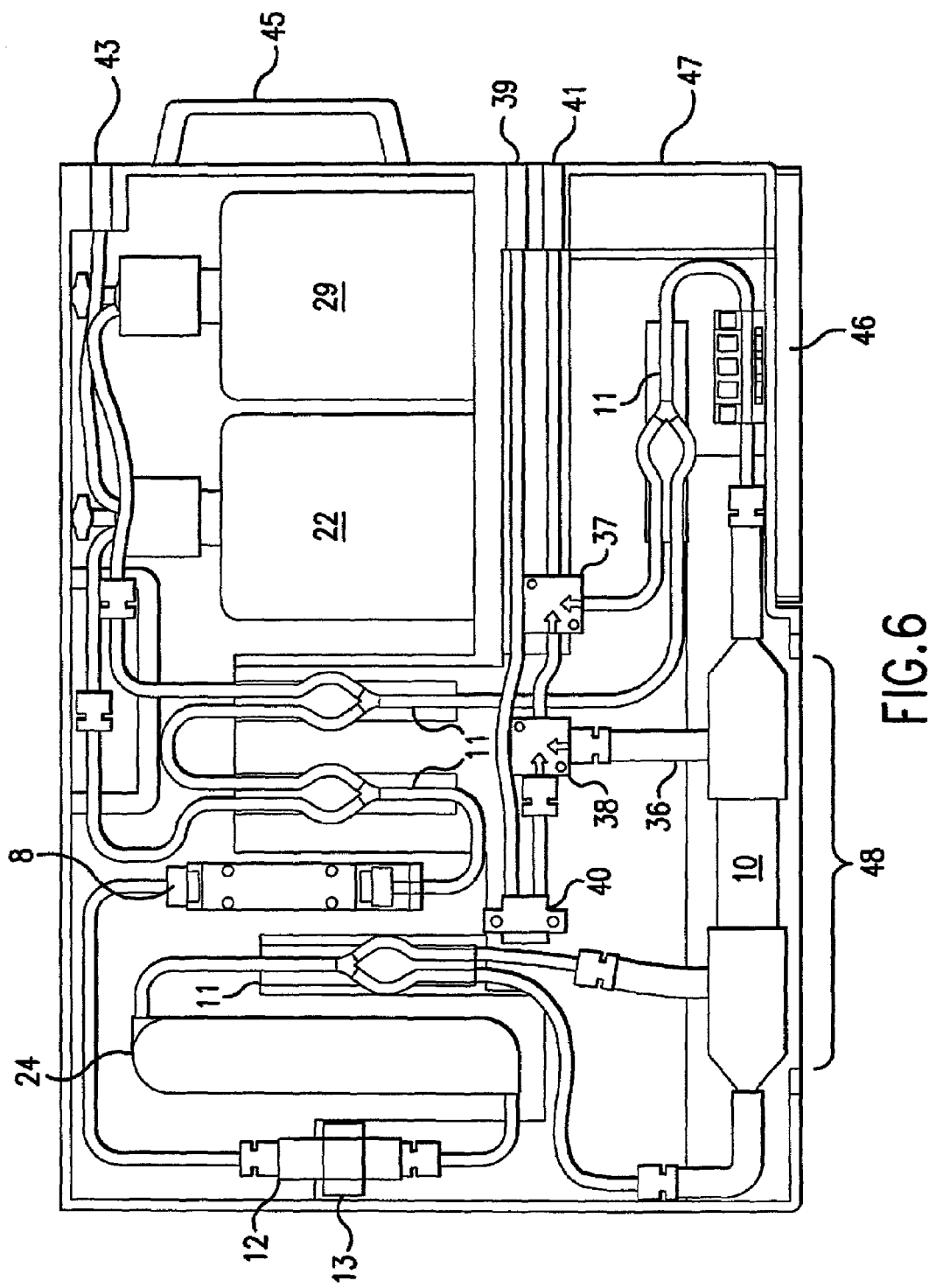
FIG. 6 is a schematic illustrating a cartridge and flowpath assembly, including an integrated automated sampling apparatus.
Figure 7:
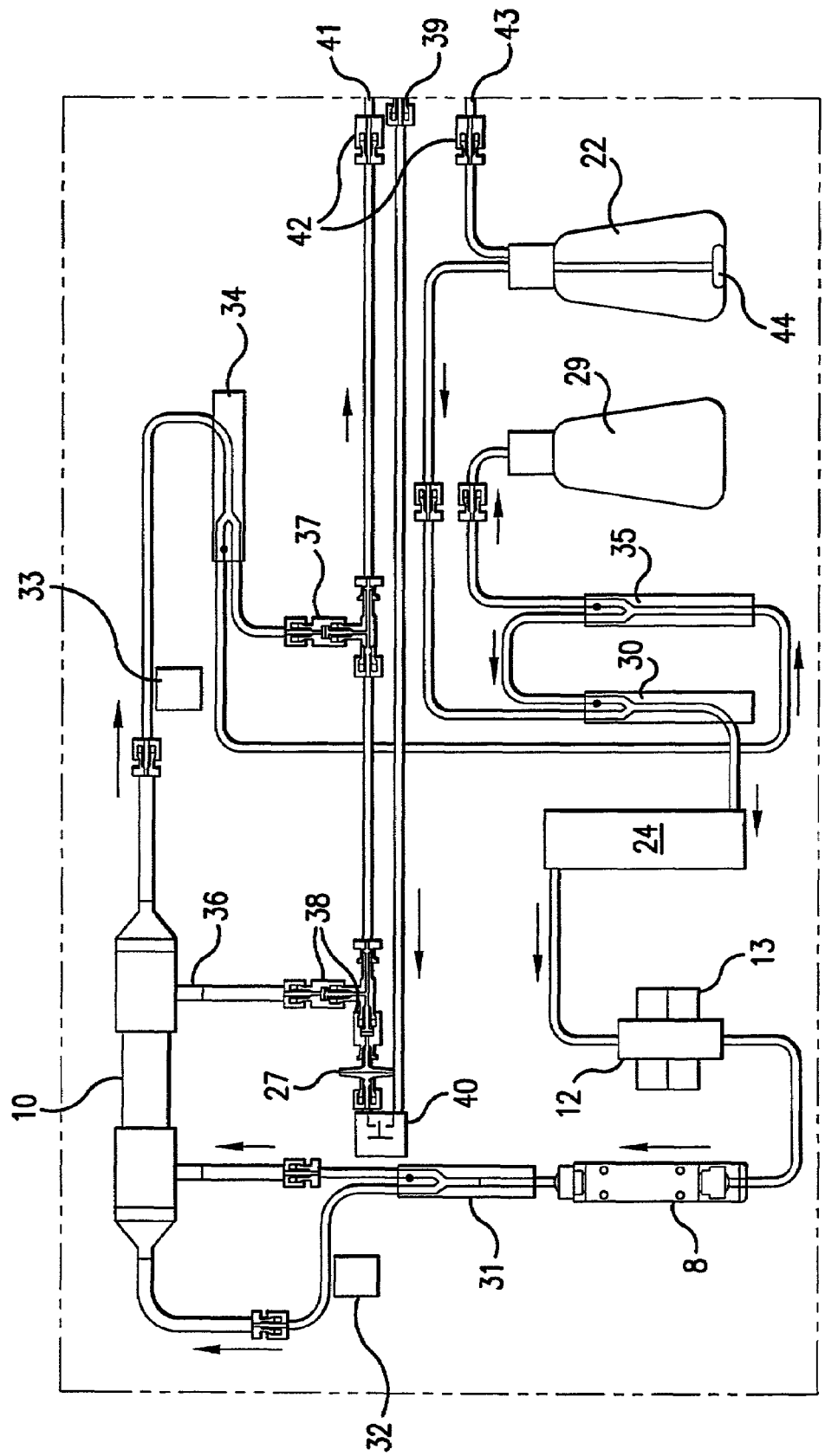
FIG. 7 is a schematic illustrating an alternate embodiment of a cartridge and flowpath assembly.
Figure 8:
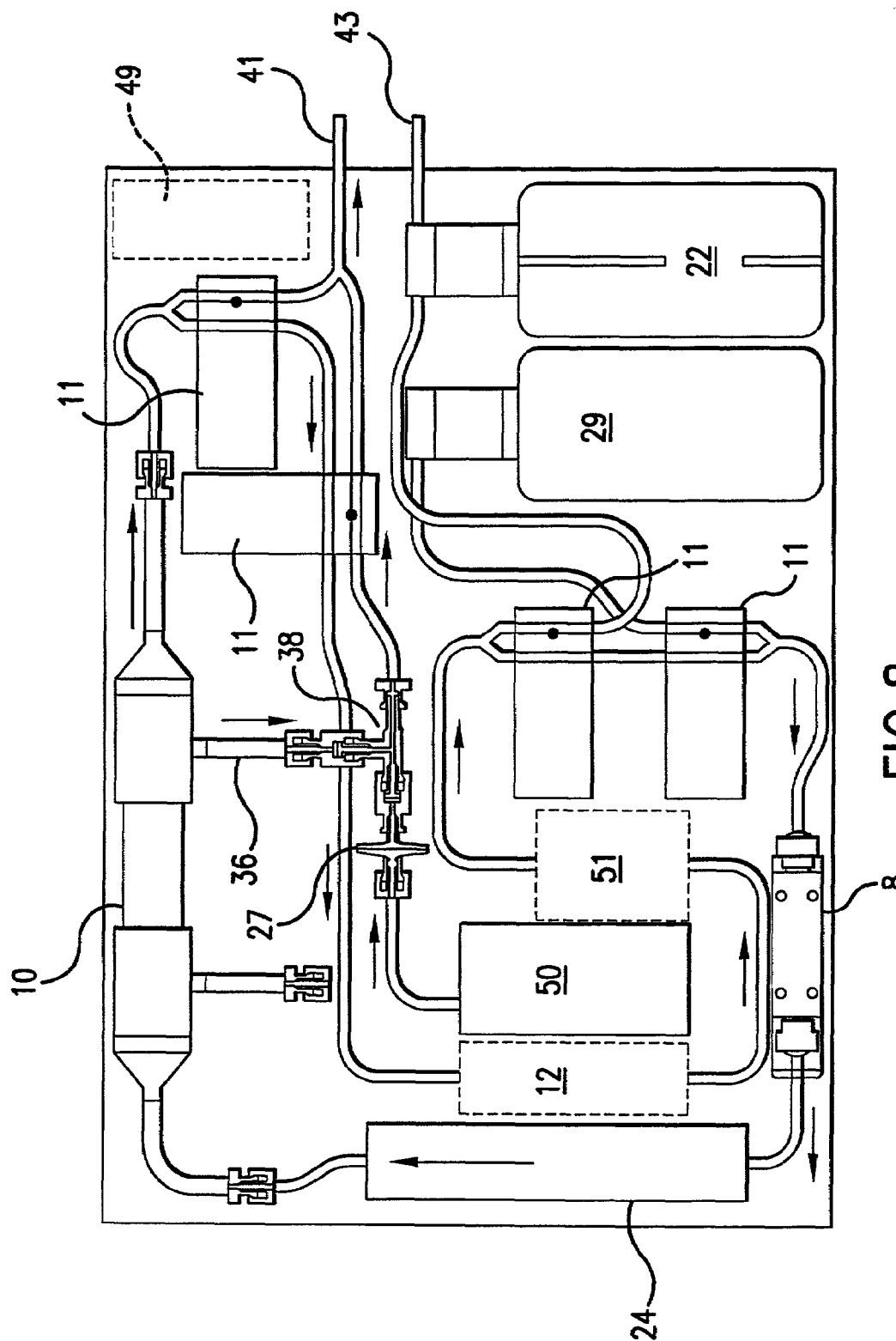
FIG. 8 is a schematic illustrating a further alternate embodiment of a cartridge and flowpath assembly.

FIGS. 6, 7, and 8 illustrate alternative embodiments of a media perfusion loop or flowpath arranged within a cartridge housing in accordance with the present invention. Referring to FIG. 7, during operation, media contained in the media reservoir 22 travels via tubing through a tubing section in contact with a first valve 30 which diverts a portion of the media to oxygenator 24. In the illustrated embodiment, the diverted media then travels through a flow cell 12 which is removably attachable to a noninvasive sensor 13. In a preferred embodiment, the flow cell comprises a drip chamber. As used herein, "noninvasive" means that the sensor operates without invading or interfering with the sterility of the perfusion loop. Noninvasive sensor 13 is preferably a pH sensor or combination pH sensor/drip chamber. The flow cell provides a selective barrier membrane which prevents proteins and other substances in the media from interfering with the detection signal. The membrane allows for easy transfer of hydrogen ions across the membrane to the detection path of the sensor. The pH sensor preferably includes LEDs and photodetectors for measuring light transmission through cell culture media. The noninvasive sensor may be an oxygen sensor or any other analyzer suitable for use in the present invention.

In FIG. 7, the media then travels through a tubing section in contact with a pump 8, then through a tubing section in contact with a second valve 31, which diverts a portion of the flow either directly to biochamber 10, or first through tubing which subjects the circulating media to a first noninvasive oxygen sensor 32 then to biochamber 10. In the illustrated embodiment, the media then flows from the biochamber 10 past a second noninvasive oxygen sensor 33 and through a tubing section in contact with a third valve 34. In the illustrated embodiment, valve 34 may divert the flow to a tubing section in contact with a fourth valve 35, which in turn diverts the flow either back through tubing in contact with first valve 30 for recirculation or to waste reservoir 29. The first, second, third, or fourth valves may be pinch valves. Alternatively, the first second, third, or fourth valves may be a diverter valve routing manifold including means for flow reversal. As illustrated, flow may also be diverted from biochamber 10, through valve 34, and through first check valve 37 integrated with a sampling apparatus for sampling the contents of the biochamber. Alternatively, flow may be diverted from biochamber 10 through side sampling port 36 and through a second check valve 38 integrated with a sampling apparatus. The tubing section in contact with the pump or valves may form a diaphragm. In alternate embodiments, the perfusion loop can include additional diverter valves and Y selector flowpath routings for cell sampling, intra-chamber media sampling, reverse flow, and numerous other applications for which diversion of flow is desired.

The sampling apparatus illustrated in FIG. 7 includes first attachment point 39 for introducing air into the sampling tubing. The air travels through a gas valve 40 to a filter 27 for sterilizing the air, then through check valve 38, where it captures a quantity of fluid from the perfusion loop and transports the fluid as a unitized sample through second attachment point 41, which may include a lure activated valve 42 as shown. The sampling apparatus is preferably automated or may be operated manually. In a preferred embodiment, samples may be diverted to a sample reservoir and maintained in a fluid between samples. The fluid between samples may be an anti-fungal fluid. In another embodiment, the automated sampling system may flush the sample line before the sample is taken, the flush being diverted to the waste reservoir for insuring a fresh sample.

In another embodiment, the fluid may be automatically diverted through a length of tubing to the cartridge front or to an analyzer located outside the incubator. Samples may be diverted from the recirculating flowpath fluid or from fluid residing in direct contact with the cells. Fluid may be automatically routed by a computer program, or a manual interface button. In another embodiment, fluid may be removed via a syringe from the manual sampling port.

In one embodiment of a biochamber, cells are grown in a space outside fibers carrying fluid through the biochamber. This space, which is sealed from the general fluid path other than across the fiber wall, is referred to as the extra-cellular space (ECS). In another biochamber embodiment, cells are grown in suspension in the absence of fibers. Samples collected through sampling port 36 may include samples from the ECS of biochamber 10. Samples collected through sampling port 36 may include a suspension of cells. Samples may also include circulating fluid from various points in the perfusion loop.

FIG. 7 also illustrates an attachment point 43 through which an injection into media reservoir 22 may be made, and an optional stir bar 44 within the media reservoir. Fluid may be automatically injected at intervals preprogrammed into the system. Programming may occur via a manual interface or via an external computer.

FIGS. 6 and 8 show alternative embodiments including alternate arrangements of several of the components illustrated in FIG. 7. FIG. 6 also includes an optional handle 45, a noninvasive LED sensor array 46 for, e.g., pH, glucose, or $O_2$ level detection and a display and control module 47, located on the cartridge outer shell. FIG. 6 further illustrates an optional cutaway 48 adjacent to the biochamber 10 for optical viewing or video monitoring of the operating biochamber.

FIG. 8 includes an internal controller 49 with a user interface, a pH sensor 51, and an internal air pump 50 for integration with the sampling apparatus. In the illustrated embodiment, pH sensor 51 may be invasive or noninvasive. In one embodiment, pH sensor 51 is a pH probe.

Oxygenator 24 may be formed by coiling a length of gas permeable silicon or similar tubing. The oxygenator may alternately be a membrane positioned over a biochamber, valve, or another component of the flowpath. In an alternate embodiment, the oxygenator may be a hollow fiber membrane oxygenator. The oxygenator is preferably exposed to ambient air within the incubator during operation. The oxygenator brackets, if used, can be any mechanical, magnetic, or other device suitable for affixing a structure to the cartridge's outer shell.

The disposable portion of the pump, i.e., the pump tubing, may be made from silicon tubing or other biocompatible or compliant tubing which includes a one way check valve on either end. In one embodiment, it is an integral portion of the unitized disposable flow path and can be sterilized as such during manufacture of the flowpath. The pump may also include a lid for holding the pump tubing in place. Such a pump may operate by using a plate to squeeze the diaphragm and displace the fluid through the one way check valves. The fluid displacement can be modulated and a varied pressure wave produced through variable electronic signals to the direct drive motor. The pump itself may be affixed to the cartridge housing. The pump may be removable from the flowpath and housing for servicing or other purposes. In one embodiment, the pump is capable of providing a fluid flow rate of about 4 mL/min to about 40 mL/min. The pump is regulated by a feedback control process in concert with flow meters.

Figure 14:
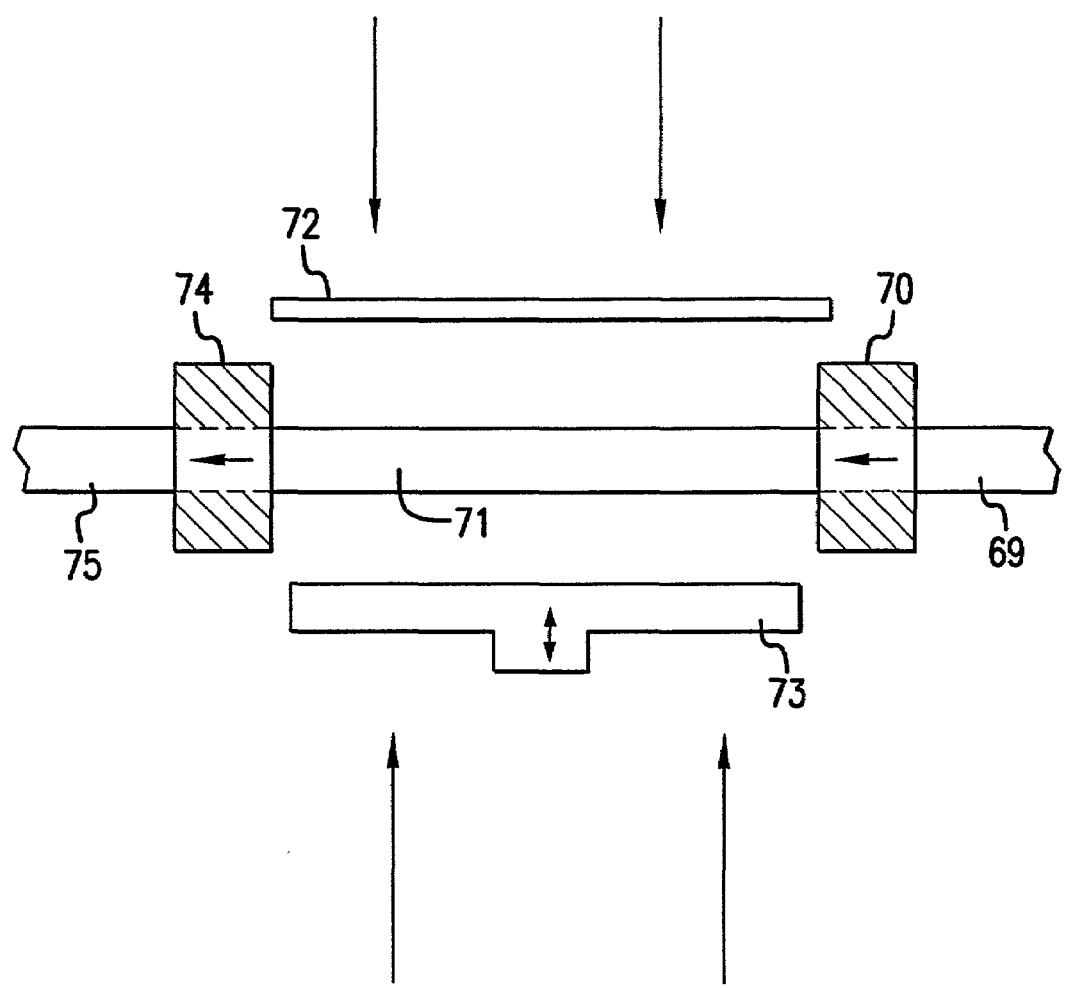
FIG. 14 depicts a pump and related structures in accordance with the present invention.

FIG. 14 illustrates one embodiment of a pump and related structures according to the invention. In FIG. 14, fluid flows through flowpath tubing 69 through a first one way flow valve 70 or check valve, into pump tubing 71. Pump actuator 73 compresses pump tubing 71 against pump lid or rigid backing 72, thereby forcing fluid from the pump tubing through a second one way flow valve 74 or check valve, into flowpath tubing 75. Flowpath tubing 69 and pump tubing 71 may be made of the same material or different materials.

Figure 15A:
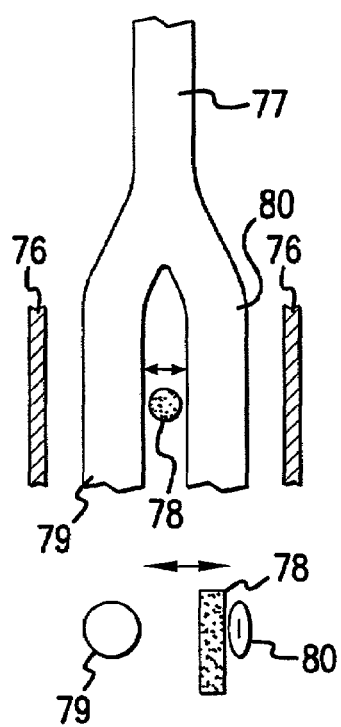
FIGS. 15A and 15B illustrate alternate embodiments of a valve for diverting media flow.
Figure 15B:
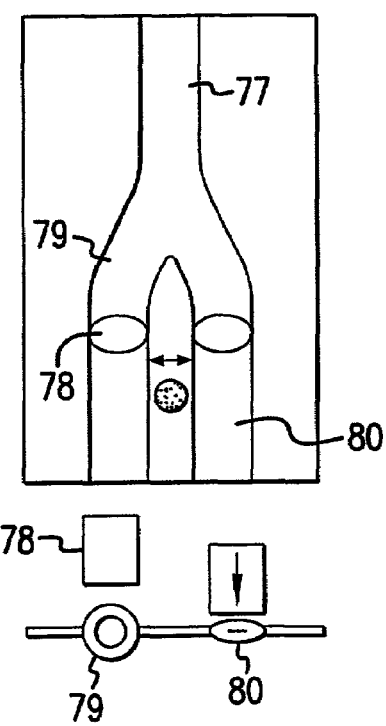

FIG. 15A illustrates an embodiment of a diverter valve suitable for use in the present invention. In the illustrated embodiment, fluid enters tubing 77 and is diverted to path 79 when actuator 78 occludes path 80 by compressing its tubing against a rigid surface 76. In FIG. 15B, fluid enters tubing 77 and is diverted to path 79 when actuator 78 occludes path 80 by compressing its tubing against surface 76. These figures provide a top view and a cross-sectional view of such valves.

The valve tubing may be flow path tubing routed through a slot in the valve. The valve tubing may be a diaphragm. The valve may be used as a diverter valve by running a flow path tube into a Y connector, then routing the two tubes through two slots on the valve. Such a mechanism only pinches one path at a time, thus allowing the user to select which path is active. Various valves and tubing or diaphragm structures may be selected by one of ordinary skill in the art given the teachings herein. The valve actuator is preferably capable of being held in position without external power. Suitable structures for attaching the unitized perfusion flow path components to the corresponding fixed structures of the cartridge housing include clips or any other fastener which sufficiently secures the path without impeding its operation.

In alternative embodiments, one or more noninvasive sensors are spectroscopy sensor arrays containing a group of LED emitters and detectors oriented such that absorption of light through the media can be examined. Such a sensor can detect frequency spectrum of the media, and provide, for example, pH level, glucose content, or $O_2$ content determinations using NIR wavelengths. The sensor can be mounted to the cartridge. In a preferred embodiment, the flow cell is a transparent tube. In another embodiment, the flow cell is positioned in a groove within a block or other body affixed to the inner surface of the cartridge outer shell. In an alternate embodiment, the sensor and flow cell are incorporated into a single unit.

The media and waste reservoirs may have a capacity of about 100 mL to about 150 mL each. However, any other size can be used and the cell culture system of the present invention can accommodate reservoirs of various fluid capacities. Fluid volumes may be selected to accommodate a variety of different cell types. Some cell types have metabolic needs in which fluid volume greater than 150 mL is preferable. Some experimental protocols suitable for use with the present invention use small volume injection of a test compound, which can be provided from a reservoir within the cartridge or injected by various other means as discussed herein. The reservoirs may include a sealable, removable lid to allow fluid to be placed into the reservoir. The lid may also include a drop tube for drawing media or other material from the reservoir and a filtered vent of about 0.2-micron or other suitable porosity to maintain sterility. The reservoirs may be made of autoclavable plastic or glass, or any suitable substance for use in holding fluid in accordance with the present invention. The vented lid is preferably made of sterilizable plastic.

Any sterile biocompatible tubing is suitable for use in the present invention. Tubing is preferably silicone. Tubing may also be a commercially available tubing such as Pharmed, Viton, Teflon, or Eagle Elastomer. In one embodiment the tubing has an inside diameter of about 3/32" and an outside diameter of about 5/32"; however, any other suitable dimensions may be used. Such tubing may be utilized for, e.g., diaphragms, or tubing in connection with valves, the oxygenator, and between components of the perfusion loop.

Figure 9:
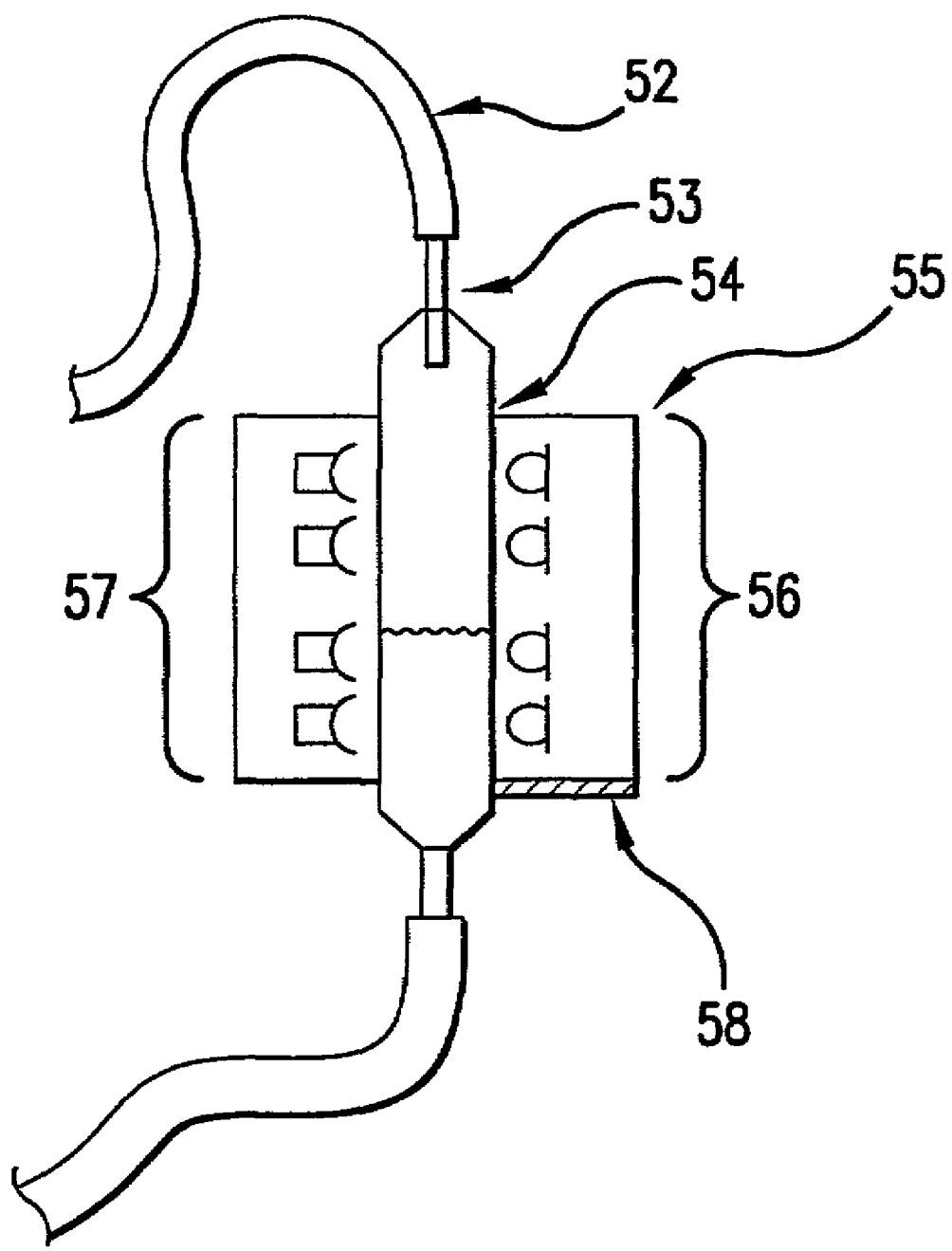
FIG. 9 depicts a drip chamber and noninvasive sensor in accordance with the invention.
Figure 10A:
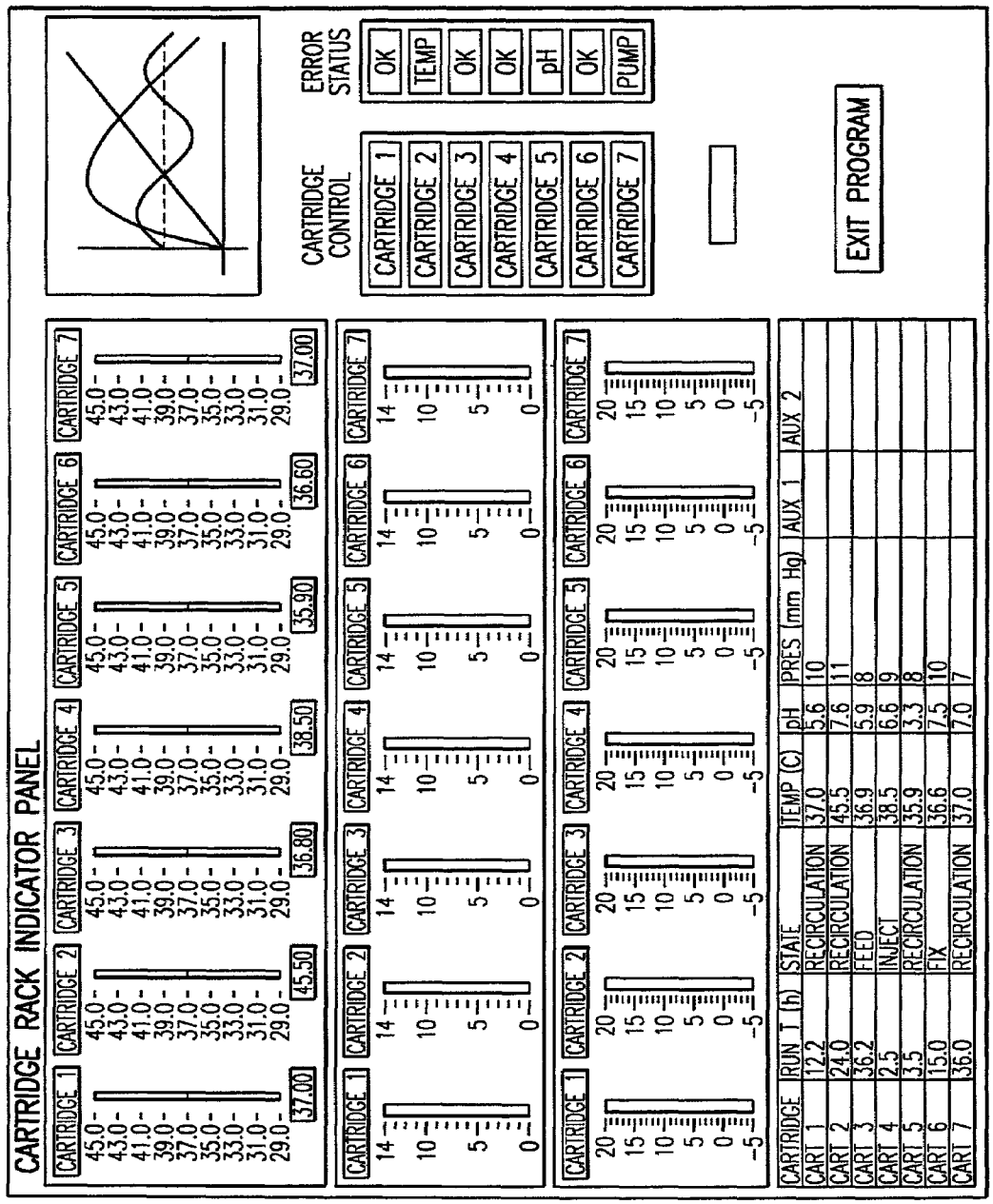
FIG. 10A shows an external cartridge controller interface.
Figure 10B:
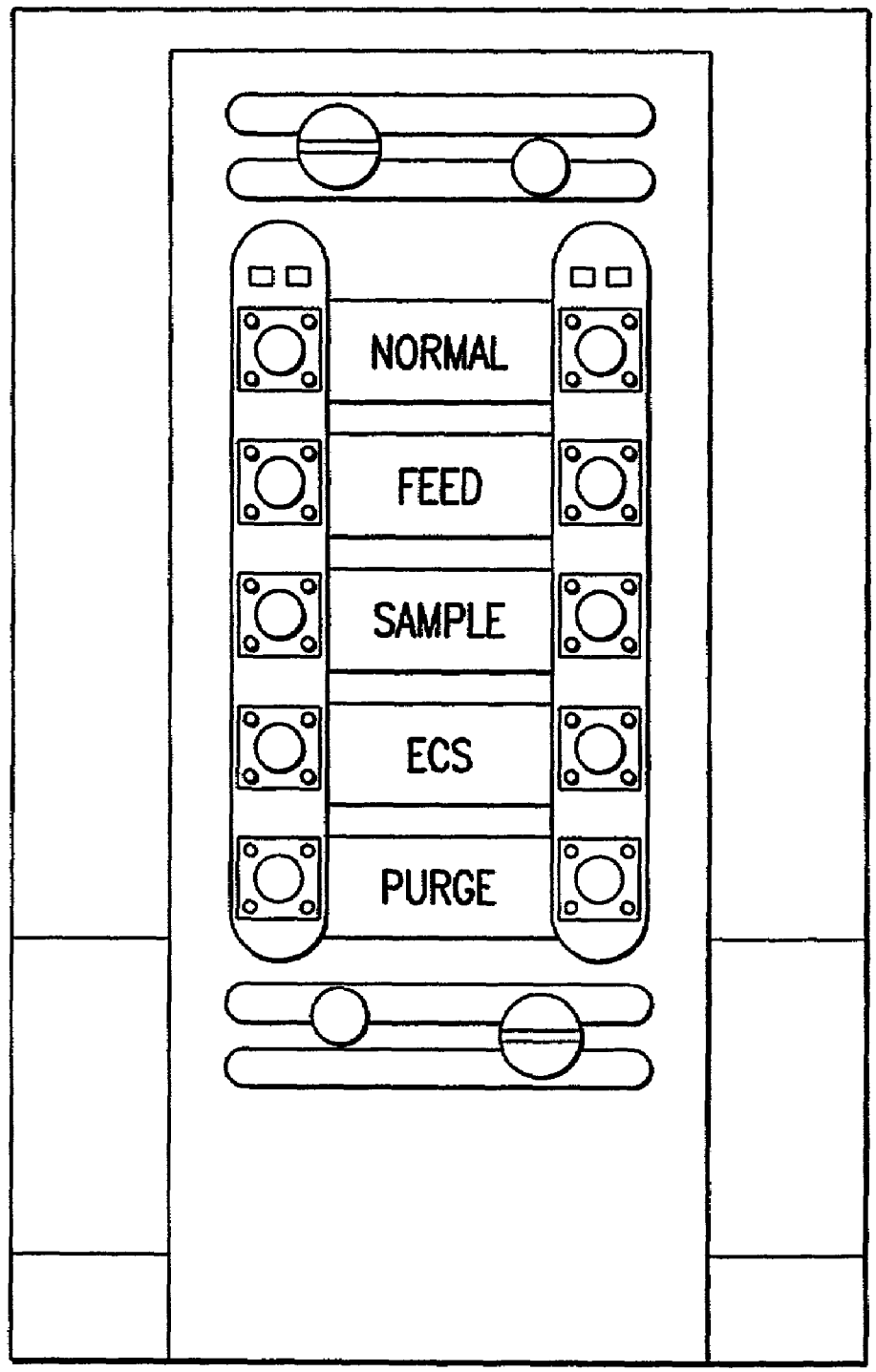
FIG. 10B shows a manual interface located on an individual cartridge.

FIG. 9 depicts one embodiment of a drip chamber and noninvasive sensor for use in the sterile media perfusion loop. During use, fluid flows through feed tube 52 and is released in discrete droplets through drip aperture 53 into partially filled, preferably transparent flow chamber 54 before exiting through tubing at the bottom of the drip chamber. As the droplets fall from the aperture, they pass through a noninvasive sensor which includes housing 55 having an emitter array 56, a photodetector array 57, and a computational chip 58. The emitter array and photodetector count the droplets and, with the computational chip, determine droplet frequency to calculate a flow rate or a volume of fluid passing during an event. The drip chamber may be positioned between the pump and the oxygenator (which precedes the cell biochamber) or located at various positions within the perfusion loop. A preferable location is downstream from the cell biochamber. Another preferred location is upstream from the pump. The sensor may be linked to a pump for providing precise injection of fluids to the recirculating media stream. Injected fluids may include media, drugs, or other additives.

Efficient collection of the tissue or cells at the completion of the culture process is an important feature of an effective cell culture system. One approach is to culture cells in a defined space without unnecessary physical barriers to recovery, so that simple elution of product results in a manageable, concentrated volume of cells amenable to final washing in a commercial, closed system or any suitable cell washer designed for the purpose. An ideal system would allow for the efficient and complete removal of all cells produced, including both adherent and non-adherent cells. Thus, various different biochambers can be used in accordance with the present invention. As used herein, a biochamber includes any bioreactor suitable for use in accordance with the invention and can include any such device for growing, maintaining, transfecting, or expanding cells or tissues. The biochamber may be, for example, a hollow fiber biochamber or bioreactor having lure fittings for attachment to the flowpath. Various biochambers and bioreactors are adaptable for use with the media flowpath assembly cartridge of the present invention given the teachings herein.

A particularly preferred biochamber is a biochamber convertible for use in static cell culture or in a cell perfusion apparatus and includes a first chamber, a cover, a seal rendering the first chamber removably connectable to the disposable cover, and at least one insert positioned between the first chamber and the disposable cover, thereby forming a second chamber. The preferred biochamber operates in two modes, open or closed. In the presealed phase or mode, the biochamber acts as a petri dish and allows for manual cell seeding and growth prior to sealing the biochamber and attachment to a flow system. In a preferred embodiment, the biochamber has a lip that acts as a sterile barrier which allows for gas diffusion but keeps bacteria out of the cell space. Cells can be grown in the ECS, which is sealed from the general fluid path other than across the membrane wall. Once sealed, the biochamber can be seeded with cells above and below the membrane insert. Ports may also be used to collect extra membrane samples throughout an ongoing experiment. In preferred embodiments, the biochamber remains horizontal in orientation and cell retrieval is carried out manually.

Figure 12:
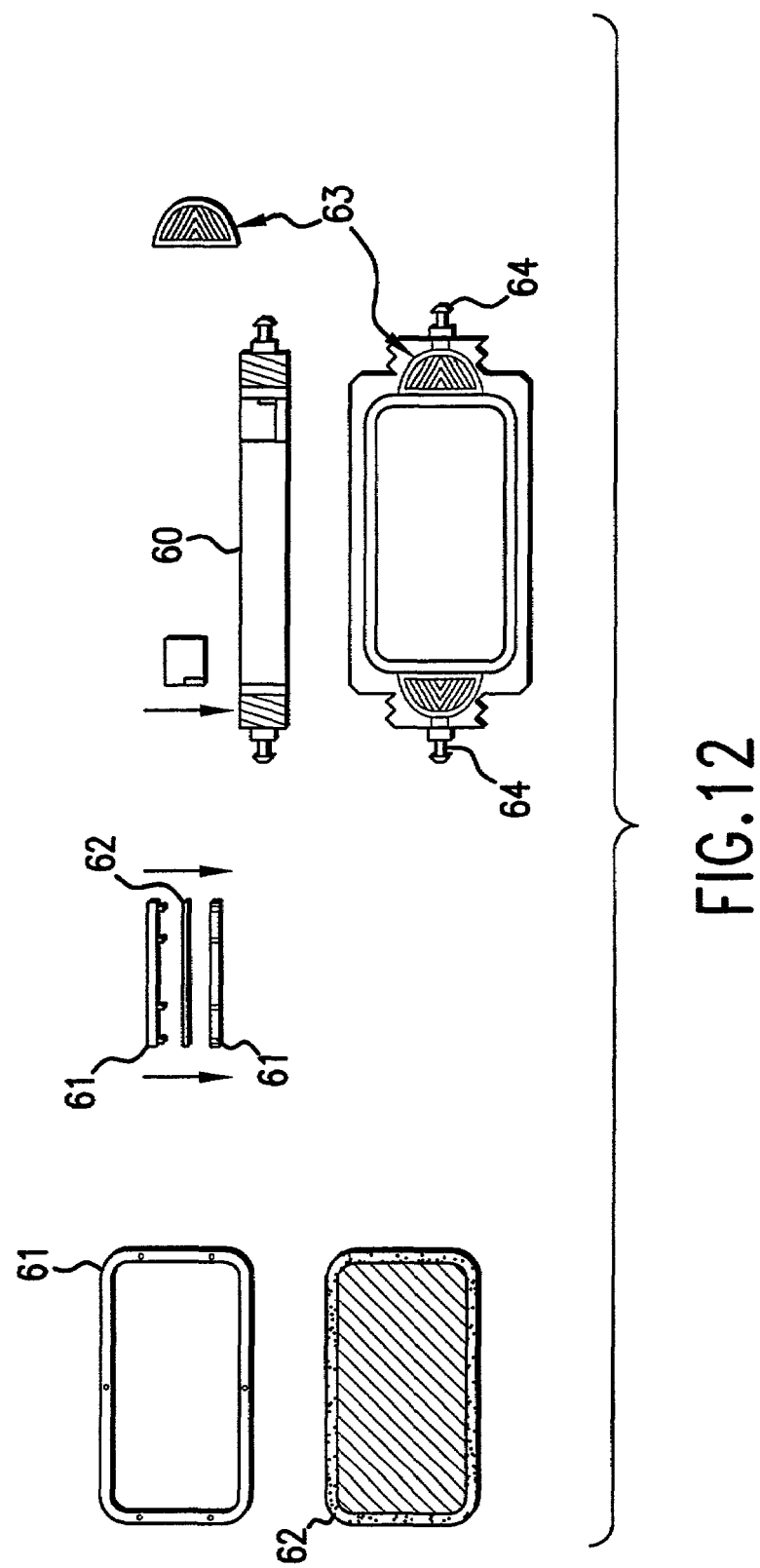
FIG. 12 illustrates separate components of an alternate biochamber embodiment.

Referring now to FIG. 11, the illustrated biochamber embodiment includes a bottom chamber 59, a cover 60, a brace 61 for holding at least one insert 62 between the bottom chamber 59 and the cover 60. The biochamber preferably includes diffusers on each end 63 for modifying pressure characteristics of incoming fluid to provide an evenly distributed flow. FIG. 12 shows components of an alternate embodiment of a biochamber according to the invention, including cover 60, braces 61, and insert 62 between two braces 61. A membrane insert is shown 62. The biochamber may accommodate a variety of selectable barrier inserts, such as hollow fibers and membranes, for cell growth. Inserts suitable for use in the present invention include semipermeable membranes. Additional inserts suitable for use in the present invention include optically reflective surfaces for enhanced contrast video microscope observation, and a variety of three-dimensional growth matrixes such as gels, elastin conduits, bio-absorbable materials, and scaffolds for improved growth and cell orientation. The biochamber can also accommodate inserts and diffusion patterns that allow active laminar flow and passive flow techniques. Inserts are preferably from about 0.001 inch to 0.1 inch thick. A grooved shelf may be provided to align the membrane assembly and provide structural support. FIG. 12 also includes connections 64 for flowpath tubing from the biochamber to the perfusion loop.

Figure 17:
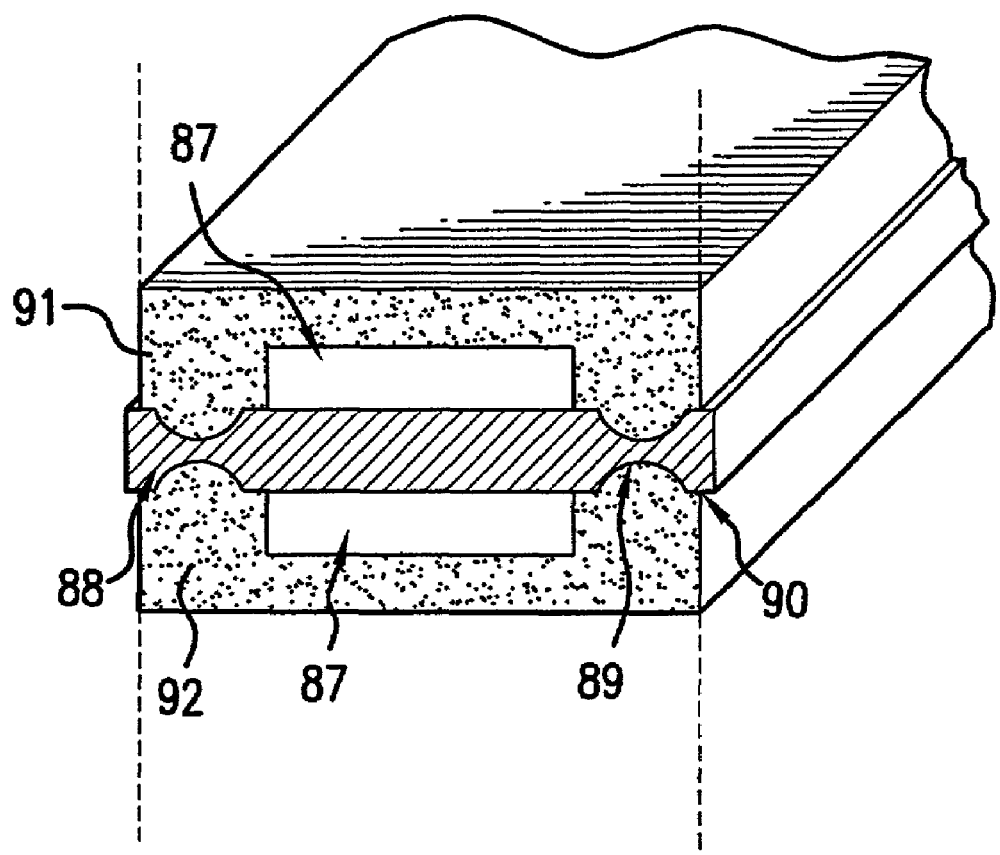
FIG. 17 illustrates a biochamber dual o-ring and air gap seal.

Referring to FIG. 17, in one embodiment a biochamber includes a seal utilizing an o-ring with dual sealing interfaces and an integral air gap to prevent contamination of the biochamber. The biochamber and o-ring sealing surfaces form an environmental seal 88, an air gap 87, and a fluid seal 89. The combination seal and air gap ensures that environmental contaminants cannot come into contact with the fluid o-ring seal 90. Fluid o-ring seal 90 can provide microscopic fluid interface channels, which might otherwise be transversed by biologic contaminants such as viruses, mycobacterium, and bacteria. The o-ring air gap is formed when the two halves 91 and 92 of the biochamber are mated and air, which has been HEPA filtered or made sterile through any suitable method, is trapped between the two o-ring interfaces. The environmental seal 88 prevents contaminants from reaching the air gap 87, which provides an area void of fluids and fluid micro channels which, if present could permit contamination or breaching of the fluid seat 90. The sealing o-ring and biochamber halves preferably form a continuous color change to signal the appropriate mating and seating of the sealing surfaces.

In alternate embodiments, the cover and base may have a color verifiable sealing surface that is established and maintained via threaded twist end caps or pressure maintenance solution. Such a sealing surface may reveal one color when the cover and base are sealed and a different color when the seal is broken. The sealing surface can include ridges for securing mid chamber inserts, the seal and inserts preferably being reversible and removable. In particularly preferred embodiments, multiple chamber ports allow access and flow to the central media chamber and to medium and cell products captive on either side of the insert barrier. The chamber ports also preferably provide fluid interfaces for automated perfusion manipulations such as sampling and injections.

Figure 13A:
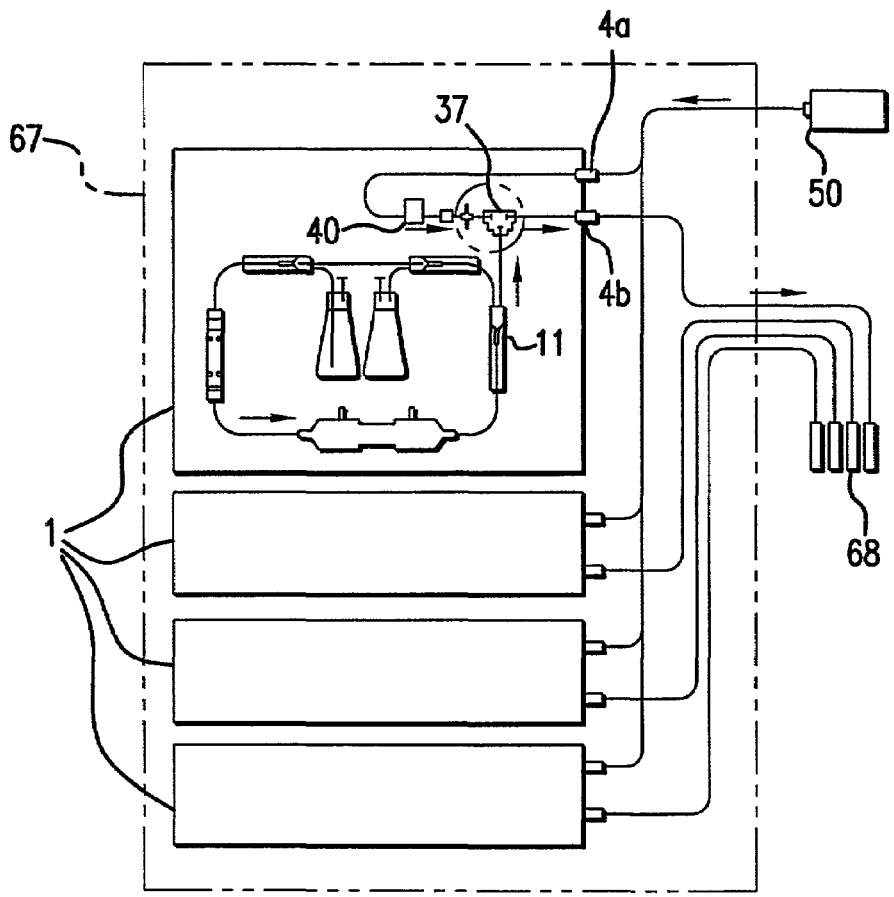
FIG. 13 is a schematic illustrating an automated sampling apparatus connected to a flowpath assembly cartridge perfusion loop in accordance with the invention.
Figure 13B:
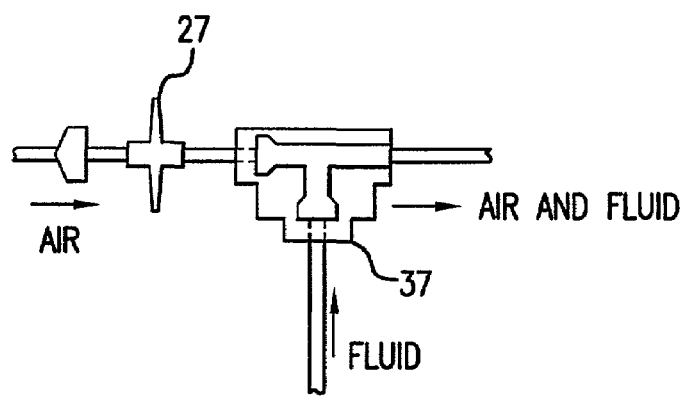

FIG. 13 is a schematic diagram of one embodiment of an automated sampling apparatus according to the present invention. The illustrated embodiment shows the sampling apparatus having an air pump 50 connected to a plurality of flowpath assembly cartridges, 1, housed within an incubator 67. Alternatively, each cartridge can have its own air pump. A sample is collected by first diverting a sample from the flowpath using a diverter valve 11. The diverter valve may be a pinch valve. The sample travels to a one way or check valve 37. Valve 40 (optional, for use with another routing or carrier fluid source; otherwise air pump 50 is used) is then opened. Air from air pump 50 passes through sterilizing filter 27 and through check valve 37, thus capturing the sample and forcing it to a collection receptacle 68. The sterilizing filter may be, for example, a 0.1 or 0.2 micron filter or a series of filters, or any other method or structure suitable to render the routing air or other carrier fluid free of biologic contaminants. The valve 40 is only required if the routing fluid is other than incubator air. A single air pump can be used with an external air source and manifold off of the air source to a plurality of cartridges. The preferred approach, however, is for each cartridge to contain the necessary hardware to perform its own sampling. The sampling apparatus may be automatically operated by pressing a button located on the cartridge. The button preferably is marked to indicate that it is for sampling. The button may be located on the front of the cartridge. In another embodiment, the sampling apparatus is operated through programmed control by an external computer. The sample may be diverted to a collection container. In one embodiment, the collection container is a tube. In another embodiment, the collection container is positioned on the front of the cartridge. The sample tubing may be flushed into the waste stream before the sample is collected for ensuring a fresh sample. In an alternate embodiment, the sample may be diverted to a sample reservoir located on a stepper motor for collection of multiple samples without operator intervention. Each sample may remain in a sample reservoir until collected for analysis, allowing for sample collection during periods of time when an operator is unavailable.

The automated sampling apparatus eliminates potential breaches of the sterile barrier and thus minimizes the risk of contamination without the use of bactericides or fungicides, which may interfere with the integrity of the sample. Potential problems associated with traditional sterile barrier culture manipulations and perturbations, such as removal of the cultures from their temperature and gas environment to room temperature and room air for processing under a sterile hood facility, are eliminated. A computer controlled sterile air pump allows integration with analysis instruments that require fixed timing by controlling sample duration and pump speed. Residual medium may be removed via a purge cycle of the collection device. In-line residual may be minimized at the point of sterile media or cell diverter and through the use of hydrophobic routing materials and surface modification. Use of periodic sterile air purge through the sample routing tube can be utilized to prevent aerosols and endotoxins from migrating back through the sample routing tube. The routing tube end when not interfaced with the collection device is preferably maintained in an antimicrobial bath. The apparatus provides a small sample (typically 0.5 to 5 mL), which is extracted from the flow path or ECS of the cell biochamber and routed via a bubble of sterilized air within the collection tube to the final collection point. For certain samples and applications any suitable alternative fluid carrier, liquid or gas, may be used to allow transport of the sample within the system and to a collection receptacle or analysis instrument.

In addition to automated sampling, the invention also permits manual cell or tissue harvest, and manual cell seeding and manipulation, under a sterile hood, with manual dual port syringe flush cell seeding. In one embodiment, a manual access port is provided for injection of cells. Injection may occur through the manual access port via a syringe or needle.

In terms of growth condition optimization and process control, the present invention provides for continuous set point maintenance of various cell culture growth parameters through sensor monitoring and feedback control of pump, valves, and other equipment suitable for a given cell culture or tissue engineering application. Data, pertaining to, for example, pH, temperature, flow rate, pump pressure, waveform, and oxygen saturation can be displayed and stored. The incubator is typically separately controllable for temperature and gas conditions. System program and status parameters, such as media flow and flow dynamics through low drip flow chamber, inline pressure sensor(s), and pump motor control, can be controlled via a computer interface allowing operator control on a PC directly or allowing protected remote communication and program modification via a modem or internet connection. Sampling increments and drug dosing can also be preprogrammed or entered directly on a separate computer or can be entered via a touch pad or other interface located on the docking station or in each cartridge.

The computer interface preferably provides a display for real-time or logged data of parameters from each cartridge including, for example, temperature, pH, flow rate, pump pulse waveform, and various scheduled events, including, for example, injection of fresh media and other fluids, and automated sampling. The pH, flow rate, pump pulse waveform, and other parameters are preferably feedback regulated from a set point selected and entered by the operator. Temperature is preferably regulated by the incubative environment. In one embodiment, the cartridge logs data without need for a separate computer. In another embodiment, a cartridge may include a digital identification when connected to the rack, for the purpose of identifying the particular experiment being run in the particular cartridge or the status of the experiment upon disconnection. Each cartridge may be keyed to a particular rack slot once operation begins, which prevents its continued operation if disconnected and replaced into an incorrect or different slot. Each cartridge preferably includes a manual interface which includes LED's to indicate the cartridge's state of operation, and which provides the operator an interface for entering set points. The interfaces also may operate while the cartridge is not in the rack.

Each cartridge preferably includes a local controller such that each noninvasive sensor generates and transmits information in the form of an electrical signal to the local controller. The signal may be transmitted by an electrical connection either directly to the local controller or first to an amplifier or transmitter and then to the controller via a communication path or bus. The communication may be transmitted serially or in parallel.

Figure 16:
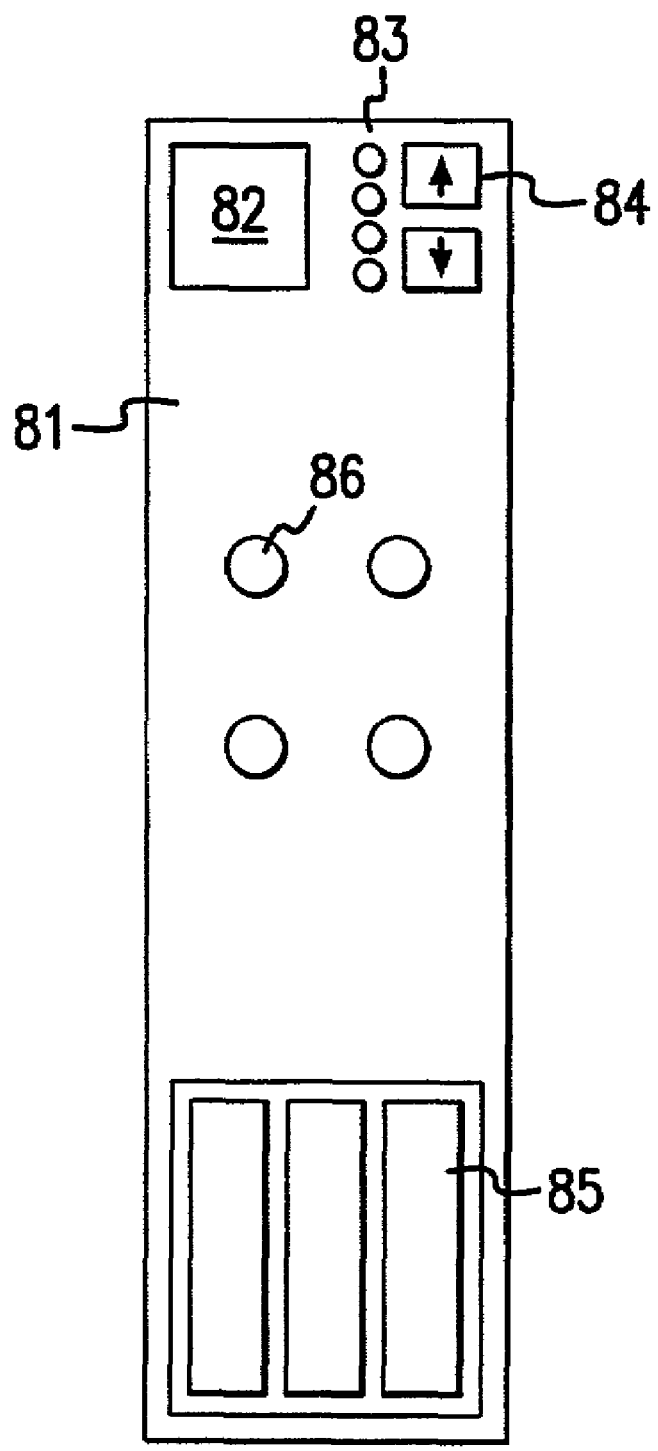
FIG. 16 illustrates the front face of a cartridge embodiment.

FIG. 16 shows one embodiment of the front face of a cartridge 81 of the present invention, including a display 82, LEDs 83, operator interface 84, sample collection tubes 85, and sites 86 for injection or sampling.

The controller includes information corresponding to a measured value with a set point which is either preprogrammed within it (such as in a chip) or can be entered using a touch pad or interface located on the cartridge or as part of a PC or other central computer system connected to the local controller. When the controller receives the signal from the sensor, it determines whether to move the process value closer to the programmed set point (i.e., change the flow rate, divert media flow, etc.) and transmits the information to the pump, altering its flow rate if necessary, or to the valve, diverting media flow if necessary or desired. This feedback control is preferably continuous throughout operation of the system. Automatic warning alarms may be utilized to alert the operator via, for example, telephone or internet connection and are preferably audible.

The local controller may be connected by a communication path to the connector located on the cartridge which in turn is connected to the connector located on the rack when the cartridge is docked. The rack can then be connected via a communication path to a central computer or controller. The communication path connected from the rack to the central computer can transmit separate information from each of a plurality of cartridges docked in the rack to the central computer. The central computer can also transmit information to each cartridge or all cartridges via a communication path from the computer to the rack and the rack to each individual cartridge. The central computer can also store and analyze information received from the cartridges.

Growth condition optimization is preferably achieved through noninvasive monitoring and precision control of numerous parameters, including flow rate, physiologic pressure and pulse wave, media addition, oxygenation and pH. In addition, sampling, fresh media addition, and drug dosing, etc., can be automated by programming a valve to divert media flow at a desired time or in accordance with a desired schedule. The process control parameters can be modified as desired to provide additional features, such as drug injection and biological function monitoring, to achieve the desired optimal results in various research and clinical contexts depending on the particular end use application.

Consistent with this growth condition optimization, each cartridge can provide a separate experiment in which any combination of configurations and events in a timed or threshold triggered fashion can be maintained, including, for example, medium re-circulation at a specified flow rate, pressure wave and shear. Once programmed, each cartridge can be operated with only a power source, such as through the attachment of a power cable or with an on board battery pack, to facilitate individual cartridge processing, analyses, or manipulation under sterile laminar flow hoods or various external analytical devices.

The cell culture system can operate in several modes. A recirculation mode keeps the media flowing through the closed perfusion loop. Alternatively, a feed/sump mode can be used in which valves divert the flowpath to supply fresh media from the media reservoir and drain waste from the perfusion loop to the waste reservoir. Switching modes may be achieved, for example, by preprogramming a predetermined volume of fresh media to be injected at predetermined intervals. Switching modes may also be achieved through the feedback control loop connected to the pH sensor. For example, the operator may input into the computer a desired pH set point. When the pH sensor detects a pH level below the set point, the system automatically injects a predetermined volume of media into the recirculating flowpath. The pH is then continually monitored and fresh media again injected as needed.

Drugs or other substances can be injected into the perfusion loop or into the biochamber for testing their effects on the growing cells and tissues. The invention further provides for automated injection of drugs or other substances directly into the media reservoir or the fluidic path leading to the desired area. Alternatively, manual injections can be performed by using a syringe and a septum attached to the media reservoir or through the manual injection site on the cartridge front face. Such manual injections may be performed with the cartridge remaining in the incubator, or at another suitable location, such as, for example, under a sterile hood during cartridge processing. Alternatively, drop by drop additions may be added and allowed to enter the media reservoir or fluidics stream.

Numerous end use applications can be achieved with the apparatus of the present invention. Numerous kinds of cells, including anchorage dependent and non anchorage dependent cells (i.e., those capable of growth in suspension) and various tissues can be grown, harvested, inoculated, and monitored through use of the present invention. More complex cell models may be achieved by using various inserts in the biochamber or through optimization of growth parameters. The system may also be used in numerous genetic and metabolic engineering applications.

Samples of fluid circulating in the loop can be extracted, as can cells or tissues growing or being maintained in the biochamber. Cells can be used in the apparatus to produce a final product of interest, such as through hybridoma production of monoclonal antibodies or other products, or cells themselves can be cultured as the final product.

When a plurality of flowpaths are in operation together in a rack, the system permits parallel optimization and scale up. An operator can make one or more adjustments to one of the flowpath loops, and quickly obtain information and assess its impact on the cells or tissues being cultured. The apparatus also permits high through put and quality assurance by providing the ability to conduct parallel experiments or processes under identical conditions. Multiple racks may also be removably connected and operated together for multiple experiments or to scale up cell production. The present invention also permits optimization of, for example, any or all of the following: cell selection, growth and viability, cell growth conditions, cell metabolism or bioproduct production, development of medium for a particular cell type for limited cell populations, processing of metabolic products, and expansion to several cell products and cell co-cultivation.

The above description and examples are only illustrative of preferred embodiments which achieve the features and advantages of the present invention, and it is not intended that the present invention be limited thereto.

The invention claimed is:

1. A cell culture apparatus for use within an incubator, said apparatus comprising:
    a rack for supporting at least one media flowpath assembly cartridge;
    at least one media flowpath assembly cartridge, said cartridge including:
    a housing, a media flowpath assembly, and a control interface;
        said media flowpath assembly including:
        a single pump for media flow;
        at least one valve adapted to prevent or divert media flow; and
        a single sterile media perfusion flowpath loop removably attachable to
        said housing without breaching flowpath sterility, said media perfusion loop being in contact with the pump and the at least one valve and containing:
    at least one biochamber;
    a gas permeable membrane;
    a media reservoir; and
    a sampling device, comprising an air pump, a sterilizing air filter, and a one-way flow valve, for capturing an aliquot of sample from the perfusion loop;
    which are in fluid communication with one another.

2. The apparatus of claim 1, wherein said housing further comprises at least one noninvasive sensor.

3. The apparatus of claim 2, further comprising a flow cell removably positionable within said noninvasive sensor.

4. The apparatus of claim 2, wherein said noninvasive sensor is a pH sensor.

5. The apparatus of claim 2, wherein said noninvasive sensor is a glucose content sensor.

6. The apparatus of claim 2, wherein said noninvasive sensor is an oxygen sensor.

7. The apparatus of claim 2, wherein said noninvasive sensor is a spectroscopy sensor.

8. The apparatus of claim 2, wherein said media flow pump is regulated by feedback control via data received from said noninvasive sensor.

9. The apparatus of claim 2, wherein said at least one valve adapted to prevent or divert media is regulated by feedback control via data received from said noninvasive sensor.

10. The apparatus of claim 1, further comprising a flow sensor.

11. The apparatus of claim 10, wherein said flow sensor comprises a drip chamber.

12. The apparatus of claim 10, wherein said flow sensor is removably positionable within a noninvasive sensor.

13. The apparatus of claim 1, wherein said gas permeable membrane comprises an oxygenator.

14. The apparatus of claim 13, wherein said oxygenator permits diffusion of oxygen from an incubator environment into the flowpath.

15. The apparatus of claim 1, wherein said cartridge housing further comprises a data interface.

16. The apparatus of claim 15, wherein said rack further comprises a data interface for integration with the data interface of the cartridge housing.

17. The apparatus of claim 1, wherein said rack further comprises a data interface for integration with an external controller.

18. The apparatus of claim 1, wherein said at least one valve adapted to prevent or divert media flow is a pinch valve.

19. The apparatus of claim 1, further comprising a sampling interface in communication with said sampling device.

20. The apparatus of claim 19, wherein said sampling interface is in communication with an electronic automated sampling device.

21. The apparatus of claim 1, wherein said media perfusion loop further comprises a waste reservoir.

22. The apparatus of claim 1 further comprising an injection interface.

23. The apparatus of claim 22, wherein said injection interface is connected to an injection fluid reservoir.

24. The apparatus of claim 22, wherein said injection interface comprises an injection membrane.

25. The apparatus of claim 1, further comprising said aliquot of sample adapted to be transported from said one way flow valve to a collection device or analysis instrument.

26. The apparatus of claim 25, wherein said one way flow valve is a check valve.

27. The apparatus of claim 1, wherein said at least one biochamber is convertible for use in static cell culture or in a cell perfusion apparatus and comprises:
 a first chamber;
 a cover;
 a seal rendering said first chamber removably connectable to said cover; and
 at least one insert positioned between the first chamber and the cover, thereby forming a second chamber.

28. The apparatus of claim 27, wherein said biochamber further comprises a diffuser.

29. The apparatus of claim 27, wherein said seal comprises two or more sealing interfaces.

30. The apparatus of claim 29, wherein said biochamber further comprises at least one air gap between said two or more sealing interfaces.

31. The apparatus of claim 29, wherein said two or more sealing interfaces are capable of indicating seating of said interfaces by a color change.

32. A cell culture apparatus according to claim 1, wherein, the rack supports a plurality of said media flowpath assembly cartridges, and each of said media flowpath assembly cartridges includes:
 a housing, a media flowpath assembly, and a control interface; said media flowpath assembly including:
 a single pump for media flow;
 at least one valve adapted to prevent or divert media flow; and
 a single sterile media perfusion flowpath loop removably attachable to said housing without breaching flowpath sterility, said media perfusion loop being in contact with the pump and the at least one valve and containing:
 at least one biochamber,
 a gas permeable membrane;
 a media reservoir, and
 a sampling device, comprising an air pump, a sterilizing air filter and a one-way flow valve for capturing an aliquot of sample from the perfusion loop;
 which are in fluid communication with one another.

33. The apparatus of claim 32, wherein each housing further comprises at least one noninvasive sensor.

34. The apparatus of claim 33, further comprising a flow cell removably positionable within each noninvasive sensor.

35. The apparatus of claim 33, wherein each noninvasive sensor is a pH sensor.

36. The apparatus of claim 33, wherein each noninvasive sensor is a glucose content sensor.

37. The apparatus of claim 33, wherein each noninvasive sensor is an oxygen sensor.

38. The apparatus of claim 33, wherein each noninvasive sensor is a spectroscopy sensor.

39. The apparatus of claim 33, wherein each media flow pump is regulated by feedback control via data received from said noninvasive sensor.

40. The apparatus of claim 33, wherein each at least one valve adapted to prevent or divert media flow is regulated by feedback control via data received from said noninvasive sensor.

41. The apparatus of claim 32, further comprising at least one flow sensor.

42. The apparatus of claim 41, wherein each flow sensor comprises a drip chamber.

43. The apparatus of claim 41, wherein each flow sensor is removably positionable within a each noninvasive sensor.

44. The apparatus of claim 32, wherein each gas permeable membrane comprises an oxygenator.

45. The apparatus of claim 44, wherein each oxygenator permits diffusion of oxygen from an incubator environment into the flowpath.

46. The apparatus of claim 32, wherein each cartridge housing further comprises a data interface.

47. The apparatus of claim 46, wherein said rack further comprises a data interface for integration with the data interface of each cartridge housing.

48. The apparatus of claim 32, wherein said rack further comprises a data interface for integration with an external controller.

49. The apparatus of claim 32, wherein each at least one valve adapted to prevent or divert media flow is a pinch valve.

50. The apparatus of claim 32, further comprising a sampling interface in communication with each sampling device.

51. The apparatus of claim 50, wherein said sampling interface is in communication with an electronic automated sampling device.

52. The apparatus of claim 32, wherein each media perfusion loop further comprises a waste reservoir.

53. The apparatus of claim 32 further comprising an injection interface.

54. The apparatus of claim 53, wherein said injection interface is connected to an injection fluid reservoir.

55. The apparatus of claim 53, wherein said injection interface comprises an injection membrane.

56. The apparatus of claim 32, further comprising a means for transporting said aliquot of sample adapted to be transported from said one way flow valve to a collection device or analysis instrument.

57. The apparatus of claim 56, wherein said each one way flow valve is a check valve.

58. The apparatus of claim 32, wherein each at least one biochamber is convertible for use in static cell culture or in a cell perfusion apparatus and comprises:
 a first chamber;
 a cover;
 a seal rendering said first chamber removably connectable to said cover; and at least one insert positioned between the first chamber and the cover, thereby forming a second chamber.

59. The apparatus of claim 58, wherein each biochamber further comprises a diffuser.

60. The apparatus of claim 58, wherein each seal comprises two or more sealing interfaces.

61. The apparatus of claim 60, wherein each biochamber further comprises at least one air gap between said two or more sealing interfaces.

62. The apparatus of claim 60, wherein said two or more sealing interfaces are capable of indicating seating of said interfaces by a color change.

63. A media flowpath assembly cartridge, comprising:
 a housing, media flowpath assembly, and a control interface, said media flowpath assembly including:
  a single pump for media flow;
  at least one valve adapted to prevent or divert media flow; and
  a single sterile media perfusion flowpath loop removably attachable to said housing without breaching flowpath sterility; said media perfusion loop being in contact with the pump and the at least one valve and containing:
   at least one biochamber;
   a gas permeable membrane;
   a media reservoir; and
   a sampling device, comprising an air pump, a sterilizing air filter, and a one-way flow valve, for capturing an aliquot of sample from the perfusion loop;
  which are in fluid communication with one another.

64. The cartridge of claim 63, further comprising a power source for stand alone operation.

65. The cartridge of claim 63, further comprising a control interface for stand alone operation.

66. The cartridge of claim 63, further comprising a control interface for operation through an external computer.

67. The cartridge of claim 63, further comprising a data interface for communication with an external controller.

68. The cartridge of claim 63, further comprising a sensor and wherein said media flow pump is regulated by feedback control via data received from said sensor.

69. The cartridge of claim 63, further comprising a sensor and wherein said at least one valve adapted to prevent or divert media is regulated by feedback control via data received from said sensor.

70. The cartridge of claim 63, wherein said gas permeable membrane permits diffusion from an incubator environment into the flowpath.

71. The apparatus of claim 63, further comprising said aliquot of sample adapted to be transported from said one way flow valve to a collection device or analysis instrument.

72. The cartridge of claim 63, further comprising an injection interface.

73. The cartridge of claim 63, further comprising a pH sensor.

74. The cartridge of claim 63, further comprising a glucose sensor.

75. The cartridge of claim 63, further comprising an oxygen sensor.

76. The cartridge of claim 63, further comprising a spectroscopy sensor.

77. The cartridge of claim 63, wherein said at least one valve adapted to prevent or divert media is a pinch valve.

78. The cartridge of claim 63, wherein said at least one biochamber is convertible for use in static cell culture or in a cell perfusion apparatus and comprises:
 a first chamber;
 a cover;
 a seal rendering said first chamber removably connectable to said cover; and
 at least one insert positioned between the first chamber and the cover, thereby forming a second chamber.

79. The cartridge of claim 78, wherein said biochamber further comprises a diffuser.

80. The cartridge of claim 78, wherein said seal further comprises two or more sealing interfaces.

81. The cartridge of claim 80, wherein said biochamber further comprises at least one air gap between said two or more sealing interfaces.

82. The cartridge of claim 80, wherein said two or more sealing interfaces are capable of indicating seating of said interfaces by a color change.

83. A cell culture apparatus for use within an incubator, said apparatus comprising:
 a means for supporting at least one flowpath assembly cartridge within said incubator;
 at least one media flowpath assembly cartridge, said cartridge including:
  a housing, a media flowpath assembly, and a control interface,
  said media flowpath assembly including:
  a single pump means for transporting fluid;
  at least one valve means for diverting fluid; and
  a single disposable sterile media perfusion loop removably attachable to said housing without breaching flowpath sterility, said media perfusion loop being in contact with the pump means and the at least one valve means, and containing:
   at least one biochamber;
   a means for diffusing oxygen into said media perfusion loop;

a media reservoir; and a sampling device, comprising an air pump, a sterilizing air filter and a one-way flow valve, for capturing an aliquot of sample from the perfusion loop;

which are in fluid communication with one another.

84. The apparatus of claim 83, wherein said pump means is regulated by feedback control via data received from a means for determining pH.

85. The apparatus of claim 83, wherein said pump means is regulated by feedback control via data received from a means for determining flow rate.

86. The apparatus of claim 83, further comprising: a means for transporting said sample from said valve for capturing an aliquot of sample to a sample collection device or analysis instrument.

87. The apparatus of claim 83, wherein said biochamber comprises:

a first chamber;

a cover;

a seal rendering said first chamber removably connectable to said cover; and at least one insert positioned between the first chamber and the cover, thereby forming a second chamber.

88. A method of culturing cells comprising:

providing a cell culture apparatus for use within an incubator, said apparatus having:

a rack for supporting at least one flowpath assembly cartridge;

at least one media flowpath assembly cartridge, said cartridge including:

a housing, a media flowpath assembly, and a control interface;

said media flowpath assembly including:

a single pump for media flow;

at least one valve adapted to prevent or divert media flow; and a single sterile media perfusion loop removably attachable to said housing without breaching flowpath sterility, said media perfusion loop being in contact with the pump and the at least one valve and containing:

at least one biochamber, a gas permeable membrane to permit gas diffusion into and out of the media perfusion loop;

a media reservoir; and a sampling device, comprising an air pump, a sterilizing air filter, and a one-way flow valve, for capturing an aliquot of sample from the perfusion loop;

which are in fluid communication with one another;

introducing a biological cell into said sterile media perfusion loop; placing said apparatus into an incubator;

controlling said incubator environment under gas and temperature to control gas and temperature conditions within said biochamber; and causing said pump to transport media through said biochamber for a sufficient time to maintain said biological cell.

89. A method of determining the physiological effects of a compound or an environmental factor on a biological cell culture comprising:

providing a cell culture apparatus for use within an incubator, said apparatus including:

a rack for supporting a plurality of flowpath assembly cartridges within said incubator;

each media flowpath assembly cartridge including:

a housing, a media flowpath assembly, and a control interface;

said media flowpath assembly including:

a single pump for media flow;

at least one valve adapted to prevent or divert media flow; and a single sterile media perfusion loop removably attachable to the housing of said cartridge without breaching flowpath sterility, said media perfusion loop being in contact with the pump and the at least one valve and containing:

at least one biochamber, a gas permeable membrane to permit gas diffusion into and out of the media perfusion loop;

a media reservoir; and a sampling device, comprising an air pump, a sterilizing air filter, and a one-way flow valve, for capturing an aliquot of sample from the perfusion loop;

which are in fluid communication with one another and with said biochamber;

introducing a biological cell into each media perfusion loop of each of said plurality of cartridges;

inserting each of said plurality of cartridges into said rack; placing said rack into an incubator;

operating said cell culture apparatus under conditions permitting each said cell to propagate, thereby producing a cell product in each perfusion loop;

introducing said compound or environmental factor into at least one but not all of said media perfusion loops; and comparing the conditions of cells or cell products in different perfusion loops, thereby determining the physiologic effects of said compound or environmental factor on a biological cell.

90. The method of claim 89, wherein said compound is a compound suspected of having pharmacological activity.

91. The method of claim 89, wherein said environmental factor is selected from the group consisting of media flow rate, shear, pH, temperature, and pump waveform.

92. The method of claim 89, wherein said compound is introduced by injection into said perfusion loop.

93. The method of claim 89, wherein said biological cell culture comprises biological tissue.

94. The method of claim 89, wherein each of said cartridges is coded via a locking means to fit into only one position in said rack.

95. The method of claim 89, further comprising entering one or more different set points into a manual interface on one or more of said cartridges.

* * * * *

UNITED STATES PATENT AND TRADEMARK OFFICE
CERTIFICATE OF CORRECTION

| | | |
|---|---|---|
| PATENT NO. | : 7,270,996 B2 | Page 1 of 1 |
| APPLICATION NO. | : 09/967995 | |
| DATED | : September 18, 2007 | |
| INVENTOR(S) | : Thomas F. Cannon et al. | |

It is certified that error appears in the above-identified patent and that said Letters Patent is hereby corrected as shown below:

In column 16, claim 1 lines 55 and 56 should be joined as a sentence and not broken into a new paragraph;

In column 16, claim 1 line 63, delete the comma after the word "valve".

In column 19, claim 63 line 61, delete the comma after the word "valve".

In column 21, claim 83 line 3, delete the comma after the word "valve".

In column 21, claim 88 line 46, delete the comma after the word "valve".

In column 22, claim 89 line 24, delete the comma after the word "valve".

Signed and Sealed this

Eighteenth Day of November, 2008

JON W. DUDAS
*Director of the United States Patent and Trademark Office*